United States Patent
Schwall et al.

(10) Patent No.: US 6,207,152 B1
(45) Date of Patent: *Mar. 27, 2001

(54) HEPATOCYTE GROWTH FACTOR RECEPTOR ANTAGONISTS AND USES THEREOF

(75) Inventors: Ralph H. Schwall, Pacifica; Kelly H. Tabor, Hillsborough, both of CA (US)

(73) Assignee: Genentech, Inc., S. San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/952,235

(22) PCT Filed: May 31, 1996

(86) PCT No.: PCT/US96/08094

§ 371 Date: Feb. 17, 1998

§ 102(e) Date: Feb. 17, 1998

(87) PCT Pub. No.: WO96/38557

PCT Pub. Date: Dec. 5, 1996

Related U.S. Application Data

(63) Continuation-in-part of application No. 08/460,368, filed on Jun. 2, 1995, now Pat. No. 5,686,292.

(51) Int. Cl.$^7$ ............................ C07K 16/18; C07K 16/28; A61K 39/395
(52) U.S. Cl. ................................. 424/130.1; 424/133.1; 424/138.1; 424/141.1; 424/143.1; 424/152.1; 424/155.1; 424/156.1; 424/174.1; 530/387.1; 530/387.3; 530/388.22; 530/388.88; 530/388.85; 530/389.1; 530/389.7; 435/7.1; 435/7.2; 435/7.21; 435/7.23
(58) Field of Search ........................ 530/388.22, 387.1, 530/387.3, 388.88, 388.85, 389.1, 389.7; 424/130.1, 133.1, 138.1, 141.1, 143.1, 152.1, 155.1, 156.1, 174.1; 435/7.1, 7.2, 7.21, 7.23

(56) References Cited

U.S. PATENT DOCUMENTS

| | | |
|---|---|---|
| 006,776 * | 1/1998 | Schwall et al. . |
| 669,971 * | 9/2000 | Schwall et al. . |
| 4,342,566 | 8/1982 | Theofilopoulos et al. . |
| 4,816,567 | 3/1989 | Cabilly et al. . |
| 5,227,158 | 7/1993 | Jardieu . |
| 5,316,921 | 5/1994 | Godowski et al. . |
| 5,328,837 | 7/1994 | Godowski et al. . |
| 5,362,716 | 11/1994 | Kmiecik et al. . |
| 5,547,856 * | 8/1996 | Godowski . |
| 5,646,036 * | 7/1997 | Schwall et al. . |
| 5,686,292 * | 11/1997 | Schwall et al. . |

FOREIGN PATENT DOCUMENTS

| | | |
|---|---|---|
| 0 567 585 B1 | 11/1993 | (EP) . |
| WO 92/05184 | 4/1992 | (WO) . |
| WO 92/13097 | 8/1992 | (WO) . |
| WO 92/20792 | 11/1992 | (WO) . |
| WO 93/15754 | 8/1993 | (WO) . |
| WO 93/23541 | 11/1993 | (WO) . |
| WO 93/23550 | 11/1993 | (WO) . |
| WO 94/04679 | 3/1994 | (WO) . |
| WO 94/06909 | 3/1994 | (WO) . |
| WO 94/29348 | 12/1994 | (WO) . |
| WO 95/01376 | 1/1995 | (WO) . |

OTHER PUBLICATIONS

*Handbook of Monoclonal Antibodies*, Ferrone et al. eds., Park Ridge, NJ:Noyes Publications, pp. 302–359 and Chapter 22 (1985).

Asami et al., "Purification and Characterization of Hepatocyte Growth Factor from Injured Liver of Carbon Tetrachloride–Treated Rats" *J. Biochem.* 109:8–13 (1991).

Bellusci et al., "Creation of an Hepatocyte Growth Factor/Scatter Factor Autocrine Loop in Carcinoma Cells Induces Invasive Properties Associated with Increased Tumorigenicity" *Oncogene* 9:1091–1099 (1994).

Boerner et al., "Production of Antigen–Specific Human Monoclonal Antibodies From In Vitro–Primed Human Splenocytes" *The Journal of Immunology* 147(1):86–95 (1991).

Bottaro et al., "Identification of the Hepatocyte Growth Factor Receptor as the c–met Proto–Oncogene Product" *Science* 251:802–804 (Feb. 15, 1991).

Brodeur et al., "Mouse–Human Myeloma Partners for the Production of Heterohybridomas" *Monoclonal Antibody Production Techniques and Applications*, New York:Marcel Dekker, Inc. pp. 51–63 (1987).

Bruggemann et al., "Designer Mice: The Production of Human Antibody Repertoires in Transgenic Animals" *Year in Immunology* 7:33–40 (1993).

Carter et al., "Humanization of an anti–p185$^{HER2}$ antibody for human cancer therapy" *Proc. Natl. Acad. Sci.* 89:4285–4289 (1992).

Chamow et al., "A Humanized, Bispecific Immunoadhesin–Antibody That Retargets CD3$^+$Effectors to Kill HIV–1–Infected Cells" *Journal of Immunology* 153:4268–4280 (1994).

Chan et al., "Identification of a Competitive HGF Antagonist Encoded by an Alternative Transcript" *Science* 254:1382–1385 (1991).

(List continued on next page.)

Primary Examiner—Nancy A. Johnson
(74) Attorney, Agent, or Firm—Piper Marbury Rudnick & Wolfe LLP; Steven B. Kelber

(57) ABSTRACT

Hepatocyte growth factor (HGF) receptor antagonists are provided. The HGF receptor antagonists include HGF receptor antibodies and fragments thereof. The HGF receptor antagonists can be employed to block binding of HGF to HGF receptors or substantially inhibit HGF receptor activation. The HGF receptor antagonists may be included in pharmaceutical compositions, articles of manufacture, or kits. Methods of treating cancer using the HGF receptor antagonists are also provided.

19 Claims, 14 Drawing Sheets

OTHER PUBLICATIONS

Chan et al., "Isoforms of Human HGF and Their Biological Activities" *Hepatocyte Growth Factor–Scatter Factor (HGF–SF) and the C–Met Receptor,* I.D. Goldberg and E.M. Rosen eds., Basel:Birkhauser Verlag pp. 67–79 (1993).

Chothia, "Domain Association in Immunoglobulin Molecules: The Packing of Variable Domains" *J. Mol. Biol.* 186:651–663 (1985).

Chothia and Lesk, "Canonical structures for the hypervariable regions of immunoglobulins" *J. Mol. Biol.* 196(4):901–917 (1987).

Cole et al., "The EBV–Hybridoma Technique and Its Application to Human Lung Cancer" *Monoclonal Antibodies and Cancer Therapy,* Reisfeld et al., New York:Alan R. Liss, Inc. pp. 77–96 (1985).

Comoglio, "The HGF Receptor and Its Ligand: Structure, Signal Transduction and Biology" *Cell Biology International* (abstract only) 18(5):375 (1994).

Comoglio, "Structure, Biosynthesis and Biochemical Properties of the HGF Receptor in Normal and Malignant Cells" *Hepatocyte Growth Factor–Scatter Factor (HGF–SF) and the C–Met Receptor,* I.D. Goldberg and E.M. Rosen eds., Basel:Birkhauser Verlag pp. 131–165 (1993).

Comoglio et al., "The Met/HGF–SF Receptor" *Positive Growth Control* (Abstract Only) 192:H215.

Cooper et al., "Amplification and Overexpression of the MET Gene in Spontaneously Transformed NIH3T3 Mouse Fibroblasts" *EMBO Journal* 5(10):2623–2628 (1986).

Crepaldi et al., "Targeting of the SF/HGF Receptor to the Basolateral Domain of Polarized Epithelial Cells" *The Journal of Cell Biology* 125(2):313–320 (1994).

David et al., "Protein Iodination with Solid State Lactoperoxidase" *Biochemistry* 13(5):1014–1021 (1974).

de Sauvage et al., "Stimulation of Megakaryocytopoiesis and Thrombopoiesis by the c–Mpl Ligand" *Nature* 369:533–538 (Jun. 16, 1994).

Defrances et al., "The Presence of Hepatocyte Growth Factor in the Developing Rat" *Development* 116:387–395 (1992).

Di Renzo et al., "Overexpression of the c–MET/HGF Receptor Gene in Human Thyroid Carcinomas" *Oncogene* 7:2549–2553 (1992).

Di Renzo et al., "Selective Expression of the Met/HGF Receptor in Human Central Nervous System Microglia" *Oncogene* 8:219–222 (1993).

Fan et al., "Blockade of Epidermal Growth Factor Receptor Function by Bivalent and Monovalent Fragments of 225 Anti–Epidermal Growth Factor Receptor Monoclonal Antibodies" *Cancer Research* 53:4322–4328 (1993).

Giordano et al., "Transfer of Motogenic and Invasive Response to Scatter Factor/Hepatocyte Growth Factor by Transfection of Human met Protooncogene" *Proc. Natl. Acad. Sci. USA* 90:649–653 (Jan. 1993).

Giordano et al., "Tyrosine Kinase Receptor Indistinguishable from the C–Met Protein" *Nature* 339:155–156 (May 11, 1989).

Goding, "Production of Monoclonal Antibodies" *Monoclonal Antibodies: Principles and Practice,* Academic Press, pp. 59–103 (1986).

Gohda et al., "Purification and Partial Characterization of Hepatocyte Growth Factor from Plasma of a Patient with Fulminant Hepatic Failure" *J. Clin. Invest.* 81:414–419 (1988).

Gorman, C., "High Efficiency Gene Transfer Into Mammalian Cells" *DNA Cloning: A Practical Approach,* Glover, D.M., ed, Washington, D.C.:IRL Press vol. 2:143–190 (1985).

Han et al., "Characterization of the DNF15S2 Locus on Human Chromosome 3: Identification of a Gene Coding for Four Kringle Domains with Homology to Hepatocyte Growth Factor" *Biochemistry* 30:9768–9780 (1991).

Harris et al., "Therapeutic Antibodies—The Coming of Age" *TIBTECH* 11:42–44 (Feb. 1993).

Hartmann et al., "A Functional Domain in the Heavy Chain of Scatter Factor/Hepatocyte Growth Factor Binds the c–Met Receptor and Induces Cell Dissociation but Not Mitogenesis" *Proc. Natl. Acad. Sci. USA* 89:11574–11578 (Dec. 1992).

Hoogenboom and Winter, "By–passing immunisation: human antibodies from synthetic repertoires of germline $V_H$ gene segments rearranged in vitro" *J. Mol. Biol.* 227:381–388 (1992).

Hunter et al., "Preparation of Iodine 131 Labelled Human Growth Hormone of High Specific Activity" *Nature* 194:495–496 (1962).

Igawa et al., "Hepatocyte Growth Factor is a Potent Mitogen for Cultured Rabbit Renal Tubular Epithelial Cells" *Biochem. & Biophys. Res. Comm.* 174(2):831–838 (Jan. 31, 1991).

Iyer et al., "Structure, Tissue–Specific Expression, and Transforming Activity of the Mouse met Protooncogene" *Cell Growth & Differentiation* pp. 87–95 (1990).

Jakobovits et al., "Analysis of Homozygous Mutant Chimeric Mice: Deletion of the Immunoglobulin Heavy–Chain Joining Region Blocks B–cell Development and Antibody Production" *Proc. Natl. Acad. Sci. USA* 90:2551–2555 (Mar. 1993).

Jakobovits et al., "Germ–line Transmission and Expression of a Human–Derived Yeast Artificial Chromosome" *Nature* 362:255–258 (Mar. 18, 1993).

Jones et al., "Replacing the Complementarity–determining Regions in a Human Antibody with Those From a Mouse" *Nature* 321:522–525 (May 29, 1986).

Kabat et al., "Sequences of Proteins of Immunological Interest", Bethesda, MD:National Institute of Health (1983).

Kohler et al., "Continuous Cultures of Fused Cells Secreting Antibody of Predefined Specificity" *Nature* 256:495–497 (Aug. 7, 1975).

Kozbor et al., "A Human Hybrid Myeloma for Production of Human Monoclonal Antibodies" *The Journal of Immunology* 133(6):3001–3005 (1984).

Lindroos et al., "Hepatocyte Growth Factor (Hepatopoietin A) Rapidly Increases in Plasma before DNA Synthesis and Liver Regeneration Stimulated by Partial Hepatectomy and Carbon Tetrachloride Administration" *Hepatology* 13(4):743–750 (1991).

Lokker et al., "Generation and Characterization of a Competitive Antagonist of Human Hepatocyte Growth Factor, HGF/NK1" *Journal of Biological Chemistry* 268(23):17145–17150 (Aug. 15, 1993).

Lokker et al., "Structure–Function Analysis of Hepatocyte Growth Factor: Identification of Variants that Lack Mitogenic Activity Yet Retain High Affinity Receptor Binding" *EMBO Journal* 11(7):2503–2510 (1992).

Mark et al., "Expression and Characterization of Hepatocyte Growth Factor Receptor–IgG Fusion Proteins" *The Journal of Biological Chemistry* 267(36):26166–26171 (Dec. 25, 1992).

Marks et al., "By–passing immunization: human antibodies from V–gene libraries displayed on phage" *J. Mol. Biol.* 222:581–597 (1991).

Matsumoto et al., "Deletion of Kringle Domains or the N–Terminal Hairpin Structure in Hepatocyte Growth Factor Results in Marked Decreases in Related Biological Activities" *Biochem. & Biophys. Res. Comm.* 181(2):691–699 (Dec. 16, 1991).

Matsumoto et al., "Hepatocyte Growth Factor is a Potent Stimulator of Human Melanocyte DNA Synthesis and Growth" *Biochem. & Biophys. Res. Comm.* 176(1):45–51 (Apr. 15, 1991).

Michalopoulos et al., "Control of Hepatocyte Replication by Two Serum Factors" *Cancer Research* 44:4414–4419 (Oct. 1984).

Miyazawa et al., "An Alternatively Processed mRNA Generated from Human Hepatocyte Growth Factor Gene" *European Journal of Biochemistry* 197:15–22 (1991).

Miyazawa et al., "Molecular Cloning and Sequence Analysis of cDNA for Human Hepatocyte Growth Factor" *Biochem. & Biophys. Res. Comm.* 163(2):967–973 (Sep. 15, 1989).

Montesano et al., "Identification of a Fibroblast–Derived Epithelial Morphogen as Hepatocyte Growth Factor" *Cell* 67:901–908 (Nov. 29, 1991).

Morrison et al., "Chimeric Human Antibody Molecules: Mouse Antigen–binding Domains with Human Constant Region Domains" *Proc. Natl. Acad. Sci. USA* 81:6851–6855 (Nov. 1984).

Munson et al., "Ligand: A Versatile Computerized Approach for Characterization of Ligand–Binding Systems" *Analytical Biochemistry* 107:220–239 (1980).

Naka et al., "Activation of Hepatocyte Growth Factor by Proteolytic Conversion of a Single Chain Form to a Heterodimer" *The Journal of Biological Chemistry* 267(28):20114–20119 (1992).

Nakamura et al., "Molecular Cloning and Expression of Human Hepatocyte Growth Factor" *Nature* 342:440–443 (Nov. 23, 1989).

Nakamura et al., "Partial Purification and Characterization of Hepatocyte Growth Factor from Serum of Hepatectomized Rats" *Biochem. & Biophys. Res. Comm.* 122:1450–1459 (Aug. 16, 1984).

Nakamura et al., "Purification and Characterization of a Growth Factor from Rat Platelets for Mature Parenchymal Hepatocytes in Primary Cultures" *Proc. Natl. Acad. Sci. USA* 83:6489–6493 (1986).

Nakamura et al., "Purification and Subunit Structure of Hepatocyte Growth Factor from Rat Platelets" *FEBS Letters* 224(2):311–316 (Nov. 1987).

Naldini et al., "Hepatocyte Growth Factor (HGF) Stimulates the Tyrosine Kinase Activity of the Receptor Encoded by the Proto–Oncogene c–MET" *Oncogene* 6:501–504 (1991).

Naldini et al., "Scatter Factor and Hepatocyte Growth Factor are Indistinguishable Ligands for the MET Receptor" *EMBO Journal* 10(10):2867–2878 (1991).

Novotny and Haber, "Structural invariants of antigen binding: comparison of immunoglobulin $V_L$–$V_H$ and $V_L$–$V_L$ domain dimers" *Proc. Natl. Acad. Sci. USA* 82(14):4592–4596 (Jul. 1985).

Nygren, H., "Conjugation of Horseradish Peroxidase to Fab Fragments with Different Homobifunctional and Heterobifunctional Cross–Linking Reagents" *The Journal of Histochemistry and Cytochemistry* 30(5):407–412 (1982).

Okajima et al., "Primary Structure of Rat Hepatocyte Growth Factor and Induction of Its mRNA During Liver Regeneration Following Hepatic Injury" *European Journal of Biochemistry* 193:375–381 (1990).

Pain et al., "Preparation of Protein A–Peroxidase Monoconjugate Using a Heterobifunctional Reagent, and its Use in Enzyme Immunoassays" *Journal of Immunological Methods* 40:219–230 (1981).

Palacios et al., "IL3–Dependent Mouse Clones That Express B–220 Surface Antigen, Contain Ig Genes in Germ–Line Configuration, and Generate B Lymphocytes In Vivo" *Cell* 41:727–734 (1985).

Park et al., "Sequence of MET Protooncogene cDNA has Features Characteristic of the Tyrosine Kinase Family of Growth–Factor Receptors" *Proc. Natl. Acad. Sci. USA* 84:6379–6383 (1987).

Ponzetto et al., "c–met is Amplified But Not Mutated in a Cell Line with an Activated met Tyrosine Kinase" *Oncogene* 6:553–559 (1991).

Ponzetto et al., "A Novel Recognition Motif for Phosphatidylinositol 3–Kinase Binding Mediates Its Association With The Hepatocyte Growth Factor/Scatter Factor Receptor" *Molecular & Cellular Biology* 13(8):4600–4608 (1993).

Prat et al., "C–Terminal Truncated Forms of Met, the Hepatocyte Growth Factor Receptor" *Molecular & Cellular Biology* 11(12):5954–5962 (1991).

Prat et al., "The Receptor Encoded by the Human c–Met Oncogene is Expressed in Hepatocytes, Epithelial Cells and Solid Tumors" *Int. J. Cancer* 49:323–328 (1991).

Presta et al., "Humanization of an Antibody Directed Against IgE" *J. Immunol.* 151(5):2623–2632 (Sep. 1, 1993).

Presta, L., "Antibody Engineering" *Curr. Op. Struct. Biol.* 2:593–596 (1992).

Riechmann et al., "Reshaping Human Antibodies for Therapy" *Nature* 332:323–327 (Mar. 24, 1988).

Rodrigues et al., "Alternative Splicing Generates Isoforms of the met Receptor Tyrosine Kinase Which Undergo Differential Processing" *Molecular & Cellular Biology* 11(6):2962–2970 (1991).

Rubin et al., "A Broad–Spectrum Human Lung bx;1Fibroblast–Derived Mitogen is a Variant of Hepatocyte Growth Factor" *Proc. Natl. Acad Sci. USA* 88:415–419 (1991).

Russell et al., "Partial Characterization of a Hepatocyte Growth Factor From Rat Platelets" *J. Cellular Physiology* 119:183–192 (1984).

Seki et al., "Isolation and Expression of cDNA for Different Forms of Hepatocyte Growth Factor from Human Leukocyte" *Biochem. and Biophys. Res. Commun.* 172(1):321–327 (Oct. 15, 1990).

Sims et al., "A Humanized CD18 Antibody Can Block Function Without Cell Destruction" *The Journal of Immunology* 151(4):2296–2308 (Aug. 1993).

Smith et al., "Cardiac Glycoside–Specific Antibodies in the Treatment of Digitalis Intoxication" *Antibodies in Human Diagnosis and Therapy* pp. 365–389 (1977).

Stoker et al., "Scatter Factor is a Fibroblast–Derived Modulator of Epithelial Cell Mobility" *Nature* 327:239–242 (May 21, 1987).

Sunitha et al., "Hepatocyte Growth Factor Stimulates Invasion Across Reconstituted Basement Membranes by a New Human Small Intestinal Cell Line" *Clin. Exp. Metastasis* 12:143–154 (1994).

Tashiro et al., "Deduced Primary Structure of Rat Hepatocyte Growth Factor and Expression of the mRNA in Rat Tissues" *Proc. Natl. Acad. Sci. USA* 87:3200–3204 (1990).

Upstate Biotechnology Inc. *Anti–human Met Monoclonal Antibodies* (product literature).

Verhoeyen et al., "Reshaping Human Antibodies: Grafting and Antilysozyme Activity" *Science* 239:1534–1536 (Mar. 25, 1988).

Weidner et al., "Scatter Factor: Molecular Characteristics and Effect on the Invasiveness of Epithelial Cells" *Journal of Cell Biology* 111:2097–2018 (Nov. 1990).

Yamada et al., "Immunohistochemistry with Antibodies to Hepatocyte Growth Factor and its Receptor Protein (c–MET) in Human Brain Tissues" *Brain Research* 637:308–312 (1994).

Zola, "Using Monoclonal Antibodies: Soluble Antigens" *Monoclonal Antibodies: A Manual of Techniques,* CRC Press, Chapter 6, pp. 147–158 (1987).

\* cited by examiner

5D5 Light Chain

```
  1 AspIleMetMetSerGlnSerProSerSerLeuThrValSerValGlyGluLysValThrValSerCysLys
  1 GACATTATGATGTCCCAGTCTCCATCCTCCCTAACTGTGTCAGTTGGAGAGAAGGTTACTGTGAGCTGCAAG

25 SerSerGlnSerLeuLeuTyrThrSerSerGlnLysAsnTyrLeuAlaTrpTyrGlnGlnLysProGlyGln
 73 TCCAGTCAGTCCCTTTTATATACTAGCAGTCAGAAGAACTACTTGGCTGGTACCAGCAGAAACCAGGTCAG

49 SerProLeuLeuIleTyrTrpAlaSerThrArgGluSerGlyValProAspArgPheThrGlySerGly
145 TCTCCTAAACTGCTGATTTACTGGGCATCCACTAGGGAATCTGGGGTCCCTGATCGCTTCACAGGCAGTGGA

73 SerGlyThrAspPheThrLeuThrIleThrSerValLysAlaAspAspLeuAlaValTyrTyrCysGlnGln
217 TCTGGGACAGATTTCACTCTCACCATCACCAGTGTGAAGGCTGACGACCTGGCAGTTTATTACTGTCAGCAA

97 TyrTyrAlaTyrProTrpThrPheGlyGlyGlyThrLysLeuGluIleLysArgThrValAlaAlaProSer
289 TATTATGCCTATCCGTGGACGTTCGGTGGAGGCACAAAGTTGGAGATCAAACGGACCGTGGCTGCACCATCT

121 ValPheIlePheProProSerAspGluGlnLeuLysSerGlyThrAlaSerValValCysLeuLeuAsnAsn
361 GTCTTCATCTTCCCGCCATCTGATGAGCAGTTGAAATCTGGAACTGCCTCTGTTGTGTGCCTGCTGAATAAC

145 PheTyrProArgGluAlaLysValGlnTrpLysValAspAsnAlaLeuGlnSerGlyAsnSerGlnGluSer
433 TTCTATCCCAGAGAGGCCAAAGTACAGTGGAAGGTGGATAACGCCCTCCAATCGGGTAACTCCCAGGAGAGT

169 ValThrGluGlnAspSerLysAspSerThrTyrSerLeuSerSerThrLeuThrLeuSerLysAlaAspTyr
505 GTCACAGAGCAGGACAGCAAGGACAGCACCTACAGCCTCAGCAGCACCCTGACGCTGAGCAAAGCAGACTAC

193 GluLysHisLysValTyrAlaCysGluValThrHisGlnGlyLeuSerSerProValThrLysSerPheAsn
577 GAGAAACACAAAGTCTACGCCTGCGAAGTCACCCATCAGGGCCTGAGCTCGCCCGTCACAAAGAGCTTCAAC

217 ArgGlyGluCys
649 AGGGGAGAGTGT
```

FIG. 1A

5D5 Heavy Chain

```
  1 GlxValGlnLeuGlnGlnSerGlyProGluLeuValArgProGlyAlaSerValLysMetSerCysArgAla
  1 SAGGTTCAGCTGCAGCAGTCTGGGCCTGAACTGGTGAGGCCTGGGGCTTCAGTGAAAATGTCCTGCAGGCT

25 SerGlyTyrThrPheThrSerTyrTyrTrpLeuHisTrpValLysGlnArgProGlyGlnGlyLeuGluTrpIle
 73 TCGGGCTATACCTTCACCAGCTACTGGTTGCACTGGGTTAAACAGAGGCCTGGACAAGGCCTTGAGTGGATT

49 GlyMetIleAspProSerAsnSerAspThrArgPheAsnProAsnPheLysAspLysAlaThrLeuAsnVal
145 GGCATGATTGATCCTTCCAATAGTGACACTAGGTTTAATCCGAACTTCAAGGACAAGGCCACATTGAATGTA

73 AspArgSerAsnThrAlaTyrMetLeuLeuSerSerLeuThrSerAlaAspSerAlaValTyrTyrCys
217 GACAGATCTTCCAACACAGCCTACATGCTGCTCAGCAGCCTGACATCTGCTGACTCTGCAGTCTATTACTGT

97 AlaThrTyrGlySerTyrValSerProLeuAspTyrTrpGlyGlnGlyThrSerValThrValSerSerAla
289 GCCACATATGGTAGCTACGTTTCCCCTCTGGACTACTGGGGTCAAGGAACCTCAGTCACCGTCTCTTCCGCC

121 SerThrLysGlyProSerValPheProLeuAlaProSerSerLysSerThrSerGlyGlyThrAlaAlaLeu
361 TCCACCAAGGGCCCATCGGTCTTCCCCCTGGCACCCTCCTCCAAGAGCACCTCTGGGGGCACAGCGGCCCTG

145 GlyCysLeuValLysAspTyrPheProGluProValThrValSerTrpAsnSerGlyAlaLeuThrSerGly
433 GGCTGCCTGGTCAAGGACTACTTCCCCGAACCGGTGACGGTGTCGTGGAACTCAGGCGCCCTGACCAGCGGC

169 ValHisThrPheProAlaValLeuGlnSerSerGlyLeuTyrSerLeuSerSerValValThrValProSer
505 GTGCACACCTTCCCGGCTGTCCTACAGTCCTCAGGACTCTACTCCCTCAGCAGCGTGGTGACCGTGCCCTCC

193 SerSerLeuGlyThrGlnThrTyrIleCysAsnValAsnHisLysProSerAsnThrLysValAspLysLys
577 AGCAGCTTGGGCACCCAGACCTACATCTGCAACGTGAATCACAAGCCCAGCAACACCAAGGTCGACAAGAAA

217 ValGluProLysSerCysAspLysThrHisThrAlaAlaPro
649 GTTGAGCCCAAATCTTGTGACAAAACTCACACAGCTGCGCCG
```

FIG. 1B

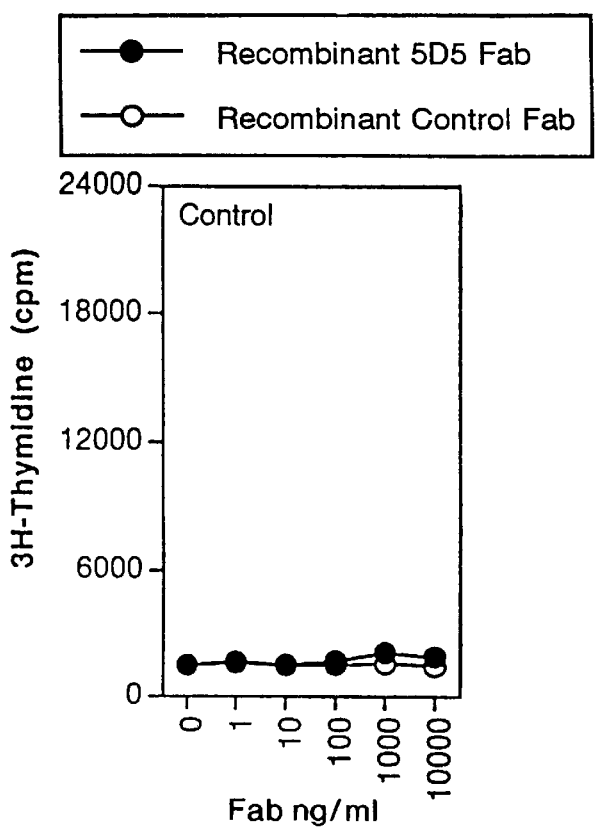
FIG. 14A
FIG. 14B
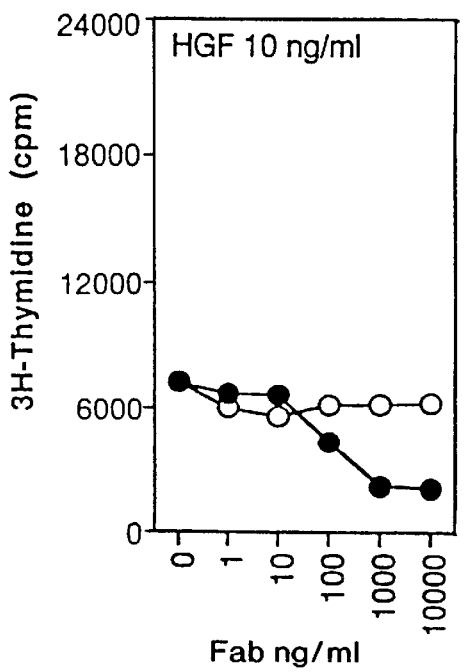
FIG. 14C
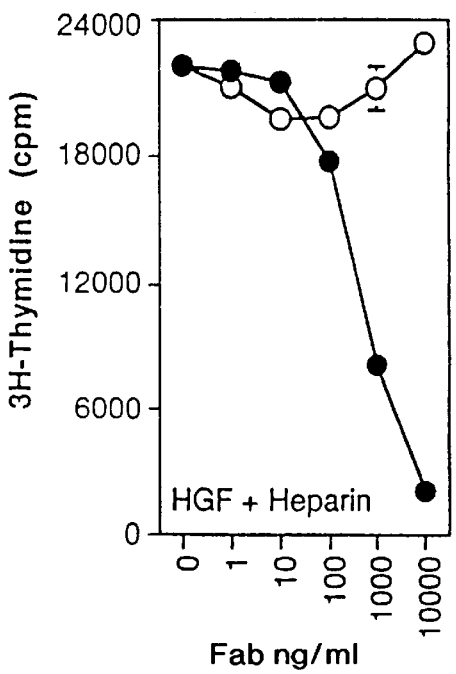
FIG. 14D

```
                             SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
        (A) LENGTH: 220 amino acids
        (B) TYPE: Amino Acid
        (D) TOPOLOGY: Linear (xi) SEQUENCE DESCRIPTION: SEQ ID NO: 1:

Asp Ile Met Met Ser Gln Ser Pro Ser Ser Leu Thr Val Ser Val
 1               5                  10                  15

Gly Glu Lys Val Thr Val Ser Cys Lys Ser Ser Gln Ser Leu Leu
                20                  25                  30

Tyr Thr Ser Ser Gln Lys Asn Tyr Leu Ala Trp Tyr Gln Gln Lys
                35                  40                  45

Pro Gly Gln Ser Pro Lys Leu Leu Ile Tyr Trp Ala Ser Thr Arg
                50                  55                  60

Glu Ser Gly Val Pro Asp Arg Phe Thr Gly Ser Gly Ser Gly Thr
                65                  70                  75

Asp Phe Thr Leu Thr Ile Thr Ser Val Lys Ala Asp Asp Leu Ala
                80                  85                  90

Val Tyr Tyr Cys Gln Gln Tyr Tyr Ala Tyr Pro Trp Thr Phe Gly
                95                  100                 105

Gly Gly Thr Lys Leu Glu Ile Lys Arg Thr Val Ala Ala Pro Ser
                110                 115                 120

Val Phe Ile Phe Pro Pro Ser Asp Glu Gln Leu Lys Ser Gly Thr
                125                 130                 135

Ala Ser Val Val Cys Leu Leu Asn Asn Phe Tyr Pro Arg Glu Ala
                140                 145                 150

Lys Val Gln Trp Lys Val Asp Asn Ala Leu Gln Ser Gly Asn Ser
                155                 160                 165

Gln Glu Ser Val Thr Glu Gln Asp Ser Lys Asp Ser Thr Tyr Ser
                170                 175                 180

Leu Ser Ser Thr Leu Thr Leu Ser Lys Ala Asp Tyr Glu Lys His
                185                 190                 195
```

```
Lys Val Tyr Ala Cys Glu Val Thr His Gln Gly Leu Ser Ser Pro
                200                 205                 210

Val Thr Lys Ser Phe Asn Arg Gly Glu Cys
                215                 220

(2) INFORMATION FOR SEQ ID NO: 2:

(i) SEQUENCE CHARACTERISTICS:
        (A) LENGTH: 230 amino acids
        (B) TYPE: Amino Acid
        (D) TOPOLOGY: Linear (xi) SEQUENCE DESCRIPTION: SEQ ID NO: 2:

Glx Val Gln Leu Gln Gln Ser Gly Pro Glu Leu Val Arg Pro Gly
 1                5                  10                  15

Ala Ser Val Lys Met Ser Cys Arg Ala Ser Gly Tyr Thr Phe Thr
                 20                 25                  30

Ser Tyr Trp Leu His Trp Val Lys Gln Arg Pro Gly Gln Gly Leu
                 35                 40                  45

Glu Trp Ile Gly Met Ile Asp Pro Ser Asn Ser Asp Thr Arg Phe
                 50                 55                  60

Asn Pro Asn Phe Lys Asp Lys Ala Thr Leu Asn Val Asp Arg Ser
                 65                 70                  75

Ser Asn Thr Ala Tyr Met Leu Leu Ser Leu Thr Ser Ala Asp
                 80                 85                  90

Ser Ala Val Tyr Tyr Cys Ala Thr Tyr Gly Ser Tyr Val Ser Pro
                 95                 100                 105

Leu Asp Tyr Trp Gly Gln Gly Thr Ser Val Thr Val Ser Ser Ala
                110                 115                 120

Ser Thr Lys Gly Pro Ser Val Phe Pro Leu Ala Pro Ser Ser Lys
                125                 130                 135

Ser Thr Ser Gly Gly Thr Ala Ala Leu Gly Cys Leu Val Lys Asp
                140                 145                 150

Tyr Phe Pro Glu Pro Val Thr Val Ser Trp Asn Ser Gly Ala Leu
                155                 160                 165

Thr Ser Gly Val His Thr Phe Pro Ala Val Leu Gln Ser Ser Gly
                170                 175                 180

Leu Tyr Ser Leu Ser Ser Val Val Thr Val Pro Ser Ser Ser Leu
                185                 190                 195

Gly Thr Gln Thr Tyr Ile Cys Asn Val Asn His Lys Pro Ser Asn
                200                 205                 210

Thr Lys Val Asp Lys Lys Val Glu Pro Lys Ser Cys Asp Lys Thr
                215                 220                 225

His Thr Ala Ala Pro
                230

(2) INFORMATION FOR SEQ ID NO: 3:

(i) SEQUENCE CHARACTERISTICS:
        (A) LENGTH: 660 base pairs
        (B) TYPE: Nucleic Acid
        (C) STRANDEDNESS: Single
        (D) TOPOLOGY: Linear (xi) SEQUENCE DESCRIPTION: SEQ ID NO: 3:

GAC ATT ATG ATG TCC CAG TCT CCA TCC TCC CTA ACT              36
Asp Ile Met Met Ser Gln Ser Pro Ser Ser Leu Thr
 1                5                  10
```

```
GTG TCA GTT GGA GAG AAG GTT ACT GTG AGC TGC AAG TCC                 75
Val Ser Val Gly Glu Lys Val Thr Val Ser Cys Lys Ser
        15                  20                  25

AGT CAG TCC CTT TTA TAT ACT AGC AGT CAG AAG AAC TAC                114
Ser Gln Ser Leu Leu Tyr Thr Ser Ser Gln Lys Asn Tyr
                30                  35

TTG GCC TGG TAC CAG CAG AAA CCA GGT CAG TCT CCT AAA                153
Leu Ala Trp Tyr Gln Gln Lys Pro Gly Gln Ser Pro Lys
        40                  45                  50

CTG CTG ATT TAC TGG GCA TCC ACT AGG GAA TCT GGG GTC                192
Leu Leu Ile Tyr Trp Ala Ser Thr Arg Glu Ser Gly Val
                55                  60

CCT GAT CGC TTC ACA GGC AGT GGA TCT GGG ACA GAT TTC                231
Pro Asp Arg Phe Thr Gly Ser Gly Ser Gly Thr Asp Phe
65                  70                  75

ACT CTC ACC ATC ACC AGT GTG AAG GCT GAC GAC CTG GCA                270
Thr Leu Thr Ile Thr Ser Val Lys Ala Asp Asp Leu Ala
        80                  85                  90

GTT TAT TAC TGT CAG CAA TAT TAT GCC TAT CCG TGG ACG                309
Val Tyr Tyr Cys Gln Gln Tyr Tyr Ala Tyr Pro Trp Thr
                95                  100

TTC GGT GGA GGC ACA AAG TTG GAG ATC AAA CGG ACC GTG                348
Phe Gly Gly Gly Thr Lys Leu Glu Ile Lys Arg Thr Val
105                 110                 115

GCT GCA CCA TCT GTC TTC ATC TTC CCG CCA TCT GAT GAG                387
Ala Ala Pro Ser Val Phe Ile Phe Pro Pro Ser Asp Glu
        120                 125

CAG TTG AAA TCT GGA ACT GCC TCT GTT GTG TGC CTG CTG                426
Gln Leu Lys Ser Gly Thr Ala Ser Val Val Cys Leu Leu
130                 135                 140

AAT AAC TTC TAT CCC AGA GAG GCC AAA GTA CAG TGG AAG                465
Asn Asn Phe Tyr Pro Arg Glu Ala Lys Val Gln Trp Lys
        145                 150                 155

GTG GAT AAC GCC CTC CAA TCG GGT AAC TCC CAG GAG AGT                504
Val Asp Asn Ala Leu Gln Ser Gly Asn Ser Gln Glu Ser
                160                 165

GTC ACA GAG CAG GAC AGC AAG GAC AGC ACC TAC AGC CTC                543
Val Thr Glu Gln Asp Ser Lys Asp Ser Thr Tyr Ser Leu
170                 175                 180

AGC AGC ACC CTG ACG CTG AGC AAA GCA GAC TAC GAG AAA                582
Ser Ser Thr Leu Thr Leu Ser Lys Ala Asp Tyr Glu Lys
        185                 190

CAC AAA GTC TAC GCC TGC GAA GTC ACC CAT CAG GGC CTG                621
His Lys Val Tyr Ala Cys Glu Val Thr His Gln Gly Leu
195                 200                 205

AGC TCG CCC GTC ACA AAG AGC TTC AAC AGG GGA GAG TGT                660
Ser Ser Pro Val Thr Lys Ser Phe Asn Arg Gly Glu Cys
        210                 215                 220

(2) INFORMATION FOR SEQ ID NO: 4:

(i) SEQUENCE CHARACTERISTICS:
        (A) LENGTH: 690 base pairs
        (B) TYPE: Nucleic Acid
        (C) STRANDEDNESS: Single
        (D) TOPOLOGY: Linear (xi) SEQUENCE DESCRIPTION: SEQ ID NO: 4:

SAG GTT CAG CTG CAG CAG TCT GGG CCT GAA CTG GTG                     36
Glx Val Gln Leu Gln Gln Ser Gly Pro Glu Leu Val
1               5                   10
```

-continued

```
AGG CCT GGG GCT TCA GTG AAA ATG TCC TGC AGG GCT TCG           75
Arg Pro Gly Ala Ser Val Lys Met Ser Cys Arg Ala Ser
         15              20                  25

GGC TAT ACC TTC ACC AGC TAC TGG TTG CAC TGG GTT AAA          114
Gly Tyr Thr Phe Thr Ser Tyr Trp Leu His Trp Val Lys
                 30              35

CAG AGG CCT GGA CAA GGC CTT GAG TGG ATT GGC ATG ATT          153
Gln Arg Pro Gly Gln Gly Leu Glu Trp Ile Gly Met Ile
     40              45              50

GAT CCT TCC AAT AGT GAC ACT AGG TTT AAT CCG AAC TTC          192
Asp Pro Ser Asn Ser Asp Thr Arg Phe Asn Pro Asn Phe
             55              60

AAG GAC AAG GCC ACA TTG AAT GTA GAC AGA TCT TCC AAC          231
Lys Asp Lys Ala Thr Leu Asn Val Asp Arg Ser Ser Asn
 65          70                      75

ACA GCC TAC ATG CTG CTC AGC AGC CTG ACA TCT GCT GAC          270
Thr Ala Tyr Met Leu Leu Ser Ser Leu Thr Ser Ala Asp
             80              85              90

TCT GCA GTC TAT TAC TGT GCC ACA TAT GGT AGC TAC GTT          309
Ser Ala Val Tyr Tyr Cys Ala Thr Tyr Gly Ser Tyr Val
                 95              100

TCC CCT CTG GAC TAC TGG GGT CAA GGA ACC TCA GTC ACC          348
Ser Pro Leu Asp Tyr Trp Gly Gln Gly Thr Ser Val Thr
105                 110                 115

GTC TCT TCC GCC TCC ACC AAG GGC CCA TCG GTC TTC CCC          387
Val Ser Ser Ala Ser Thr Lys Gly Pro Ser Val Phe Pro
             120                 125

CTG GCA CCC TCC TCC AAG AGC ACC TCT GGG GGC ACA GCG          426
Leu Ala Pro Ser Ser Lys Ser Thr Ser Gly Gly Thr Ala
130                 135                 140

GCC CTG GGC TGC CTG GTC AAG GAC TAC TTC CCC GAA CCG          465
Ala Leu Gly Cys Leu Val Lys Asp Tyr Phe Pro Glu Pro
             145                 150                 155

GTG ACG GTG TCG TGG AAC TCA GGC GCC CTG ACC AGC GGC          504
Val Thr Val Ser Trp Asn Ser Gly Ala Leu Thr Ser Gly
                 160                 165

GTG CAC ACC TTC CCG GCT GTC CTA CAG TCC TCA GGA CTC          543
Val His Thr Phe Pro Ala Val Leu Gln Ser Ser Gly Leu
     170                 175                 180

TAC TCC CTC AGC AGC GTG GTG ACC GTG CCC TCC AGC AGC          582
Tyr Ser Leu Ser Ser Val Val Thr Val Pro Ser Ser Ser
                 185                 190

TTG GGC ACC CAG ACC TAC ATC TGC AAC GTG AAT CAC AAG          621
Leu Gly Thr Gln Thr Tyr Ile Cys Asn Val Asn His Lys
195                 200                 205

CCC AGC AAC ACC AAG GTC GAC AAG AAA GTT GAG CCC AAA          660
Pro Ser Asn Thr Lys Val Asp Lys Lys Val Glu Pro Lys
         210                 215                 220

TCT TGT GAC AAA ACT CAC ACA GCT GCG CCG                     690
Ser Cys Asp Lys Thr His Thr Ala Ala Pro
                 225             230
```

HEPATOCYTE GROWTH FACTOR RECEPTOR ANTAGONISTS AND USES THEREOF

RELATED APPLICATIONS

This application is a continuation-in-part application of U.S. application Ser. No. 08/460,368 filed Jun. 2, 1995, (now U.S. Pat. No. 5,686,292) the contents of which are incorporated herein by reference.

FIELD OF THE INVENTION

This application relates to hepatocyte growth factor receptor antagonists. The application also relates to the use of the antagonists in therapy or diagnosis of particular pathological conditions in mammals, including cancer.

BACKGROUND OF THE INVENTION

Hepatocyte growth factor ("HGF") functions as a growth factor for particular tissues and cell types. HGF was identified initially as a mitogen for hepatocytes [Michalopoulos et al., Cancer Res., 44:4414–4419 (1984); Russel et al., J. Cell. Physiol., 119:183–192 (1984); Nakamura et al., Biochem. Biophys. Res. Comm., 122:1450–1459 (1984)]. Nakamura et al., supra, reported the purification of HGF from the serum of partially hepatectomized rats. Subsequently, HGF was purified from rat platelets, and its subunit structure was determined [Nakamura et al., Proc. Natl. Acad. Sci. USA, 83:6489–6493 (1986); Nakamura et al., FEBS Letters, 224:311–316 (1987)]. The purification of human HGF ("huHGF") from human plasma was first described by Gohda et al., J. Clin. Invest., 81:414–419 (1988).

Both rat HGF and huHGF have been molecularly cloned, including the cloning and sequencing of a naturally occurring variant lacking 5 amino acids designated "delta5 HGF" [Miyazawa et al., Biochem. Biophys. Res. Comm., 163:967–973 (1989); Nakamura et al., Nature, 342:440–443 (1989); Seki et al, Biochem. Biophys. Res. Commun., 172:321–327 (1990); Tashiro et al., Proc. Natl. Acad. Sci. USA, 87:3200–3204 (1990); Okajima et al., Eur. J. Biochem., 193:375–381 (1990)].

The mature form of huHGF, corresponding to the major form purified from human serum, is a disulfide linked heterodimer derived by proteolytic cleavage of the human pro-hormone between amino acids R494 and V495. This cleavage process generates a molecule composed of an α-subunit of 440 amino acids ($M_r$ 69 kDa) and a β-subunit of 234 amino acids ($M_r$ 34 kDa). The nucleotide sequence of the huHGF cDNA reveals that both the α- and the β-chains are contained in a single open reading frame coding for a pre-pro precursor protein. In the predicted primary structure of mature huHGF, an interchain S-S bridge is formed between Cys 487 of the α-chain and Cys 604 in the β-chain [see Nakamura et al., Nature, supra]. The N-terminus of the α-chain is preceded by 54 amino acids, starting with a methionine group. This segment includes a characteristic hydrophobic leader (signal) sequence of 31 residues and the prosequence. The α-chain starts at amino acid (aa) 55, and contains four kringle domains. The kringle 1 domain extends from about aa 128 to about aa 206, the kringle 2 domain is between about aa 211 and about aa 288, the kringle 3 domain is defined as extending from about aa 303 to about aa 383, and the kringle 4 domain extends from about aa 391 to about aa 464 of the α-chain.

The definition of the various kringle domains is based on their homology with kringle-like domains of other proteins (such as prothrombin and plasminogen), therefore, the above limits are only approximate. To date, the function of these kringles has not been determined. The β-chain of huHGF shows high homology to the catalytic domain of serine proteases (38% homology to the plasminogen serine protease domain). However, two of the three residues which form the catalytic triad of serine proteases are not conserved in huHGF. Therefore, despite its serine protease-like domain, huHGF appears to have no proteolytic activity, and the precise role of the β-chain remains unknown. HGF contains four putative glycosylation sites, which are located at positions 294 and 402 of the 60-chain and at positions 566 and 653 of the β-chain.

Comparisons of the amino acid sequence of rat HGF with that of huHGF have revealed that the two sequences are highly conserved and have the same characteristic structural features. The length of the four kringle domains in rat HGF is exactly the same as in huHGF. Furthermore, the cysteine residues are located in exactly the same positions, an indication of similar three-dimensional structures [Okajima et al., supra; Tashiro et al., supra].

In a portion of cDNA isolated from human leukocytes, in-frame deletion of 15 base pairs was observed. Transient expression of the cDNA sequence in COS-1 cells revealed that the encoded HGF molecule (delta5 HGF) lacking 5 amino acids in the kringle 1 domain was fully functional [Seki et al., supra].

A naturally occurring huHGF variant has been identified which corresponds to an alternative spliced form of the huHGF transcript containing the coding sequences for the N-terminal finger and first two kringle domains of mature huHGF [Chan et al., Science, 254:1382–1385 (1991); Miyazawa et al., Eur. J. Biochem., 197:15–22 (1991)]. This variant, designated HGF/NK2, has been proposed by some investigators to be a competitive antagonist of mature huHGF. Hartmann et al. have reported, however, that HGF/NK2 may retain the ability to cause MDCK cells to scatter [Hartmann et al., Proc. Natl. Acad. Sci., 89:11574–11578 (1992)].

Another HGF variant, designated HGF/NK1, has also been reported to act as a competitive antagonist of HGF [Lokker et al., J. Biol. Chem., 268:17145–17150 (1993); Lokker et al., EMBO J., 11:2503–2510 (1992)]. That HGF/NK1 molecule, containing the N-terminal hairpin and the first kringle domain, was found to block binding of HGF to the HGF receptor on A549 human lung carcinoma cells. It was also found, however, that certain concentrations of the HGF/NK1 induced a detectable increase in receptor tyrosine phosphorylation in the A549 cells, suggesting some agonistic activity. Accordingly, it is believed that the agonist or antagonist action of HGF/NK1 may be dependent upon cell type.

HGF and HGF variants are described further in U.S. Pat. Nos. 5,227,158, 5,316,921. and 5,328,837.

A high affinity receptor for HGF has been identified as the product of the c-Met proto-oncogene [Bottaro et al., Science, 251:802–804 (1991); Naldini et al., Oncogene, 6:501–504 (1991); WO 92/13097 published Aug. 6, 1992; WO 93/15754 published Aug. 19, 1993]. This receptor is usually referred to as "c-Met" or "p190$^{MET}$" and typically comprises, in its native form, a 190-kDa heterodimeric (a disulfide-linked 50-kDa α-chain and a 145-kDa β-chain) membrane-spanning tyrosine kinase protein [Park et al., Proc. Natl. Acad. Sci. USA, 84:6379–6383 (1987)]. Several truncated forms of the c-Met receptor have also been described [WO 92/20792; Prat et al., Mol. Cell. Biol., 11:5954–5962 (1991)].

The binding activity of HGF to c-Met is believed to be conveyed by a functional domain located in the N-terminal portion of the HGF molecule, including the first two kringles [Matsumoto et al., *Biochem. Biophys. Res. Commun.*, 181:691–699 (1991); Hartmann et al., *Proc. Natl. Acad. Sci.*, 89:11574–11578 (1992); Lokker et al., *EMBO J.*, 11:2503–2510 (1992); Lokker and Godowski, *J. Biol. Chem.*, 268:17145–17150 (1991)]. The c-Met protein becomes phosphorylated on tyrosine residues of the 145-kDa β-subunit upon HGF binding.

Certain antibodies to this HGF receptor have been reported in the literature. Several such antibodies are described below.

Prat et al., *Mol. Cell. Biol.*, supra, describe several monoclonal antibodies specific for the extracellular domain of the β-chain encoded by the c-Met gene [see also, WO 92/20792]. The monoclonal antibodies were selected following immunization of Balb/c mice with whole living GTL-16 cells (human gastric carcinoma cell line) overexpressing the Met protein. The spleen cells obtained from the immunized mice were fused with Ag8.653 myeloma cells, and hybrid supernatants were screened for binding to GTL-16 cells. Four monoclonal antibodies, referred to as DL-21, DN-30, DN-31 and DO-24, were selected.

Prat et al., *Int. J. Cancer*, 49:323–328 (1991) describe using anti-c-Met monoclonal antibody DO-24 for detecting distribution of the c-Met protein in human normal and neoplastic tissues [see, also. Yamada et al., *Brain Research*, 637:308–312 (1994)]. The murine monoclonal antibody DO-24 was reported to be an IgG2a isotype antibody.

Crepaldi et al., *J. Cell Biol.*, 125: 313–320 (1994) report using monoclonal antibodies DO-24 and DN-30 [described in Prat et al., *Mol. Cell. Biol.*, supra] and monoclonal antibody DQ-13 to identify subcellular distribution of HGF receptors in epithelial tissues and in MDCK cell monolayers. According to Crepaldi et al., monoclonal antibody DQ-13 was raised against a peptide corresponding to nineteen COOH-terminal amino acids (from $Ser^{372}$ to $Ser^{1390}$) of the human c-Met sequence.

A monoclonal antibody specific for the cytoplasmic domain of human c-Met has also been described [Bottaro et al., supra].

Several of the monoclonal antibodies referenced above are commercially available from Upstate Biotechnology Incorporated, Lake Placid, N.Y. Monoclonal antibodies DO-24 and DL-21, specific for the extracellular epitope of c-Met, are available from Upstate Biotechnology Incorporated. Monoclonal antibody DQ-13, specific for the intracellular epitope of c-Met, is also available from Upstate Biotechnology Incorporated.

In addition to binding c-Met, it is recognized that HGF binds to some heparin and heparan sulfate proteoglycans which are present on cell surfaces or in extracellular matrices [Rouslahti et al., *Cell*, 64:867–869 (1991); Lyon et al., *J. Biol. Chem.*, 269:11216–11223 (1994)]. Heparan sulfate is a glycosaminoglycan similar in composition and structure to heparin and is found on many mammalian cell surfaces. Various hypotheses have been proposed to explain the role of heparin and heparan sulfate proteoglycans ("HSPGs") in the regulation of certain growth factor activity. For example, it has been hypothesized that upon binding heparin or HSPGs, certain growth factors may have a more favorable conformation for binding to their respective high affinity receptors [Lindahl et al., *Annual Rev. Biochem.*, 47:385–417 (1995)]; that HSPGs may serve as docking sites for certain growth factors facilitating the presentation of ligand to its high affinity receptor [Yayon et al., *Cell*, 64:841–848 (1991); Moscatelli et al., *J. Biol. Chem.*, 267:25803–25809 (1992); Nugent et al., *Biochemistry.* 31:8876–8883 (1992)]; and that HSPGs may promote ligand dimerization facilitating receptor activation [Ornitz et al., *Mol. Cell. Biol.*, 12:240–247 (1992); Spivak-Kroizman et al., *Cell*, 79:1015–1024 (1994)]. It has further been postulated that certain growth factors are more stable or resistant to proteolytic activity [Damon et al., *J. Cell. Physiol.*, 138:221–226 (1989); Mueller et al., *J. Cell. Physiol.* 140:439–448 (1989); Rosengart et al., *Biochem. Biophys. Res. Commun.*, 152:432–440 (1998)] and denaturation [Copeland et al., *Arch. Biochem. Biophys.*, 289:53–61 (1994)] when bound to heparin. Coincubation of HGF with soluble heparin and other heparin-like molecules has been reported to promote dimerization/oligomerization of HGF and to potentiate HGF mitogenic activity. [see, e.g., WO 94/09969 published Mar. 16, 1995; Zioncheck et al., *J. Biol. Chem.*, 270:16871–16878 (1995)].

Mizuno et al. describe some experiments which attempted to locate heparin-binding sites within the HGF molecule [Mizuno et al., *J. Biol. Chem.*, 29:1131–1136 (1994)]. Mizuno et al. constructed variously deleted mutant HGFs [d-K1 (deletion of first kringle domain); d-K2 (deletion of second kringle domain); d-K3 (deletion of third kringle domain); d-K4 (deletion of fourth kringle domain); d-beta (deletion of beta chain); d-H (deletion of N-terminal hairpin loop); and HK1K2 (consisting of N-terminal hairpin loop and the first and second kringle domains)] and examined their respective binding to an immobilized heparin column. The reference reports that the d-H and d-K2 mutants exhibited decreased binding to heparin affinity columns, while the native HGF and the other constructed HGF mutants tightly bound to the heparin columns.

Various biological activities have been described for HGF and its c-Met receptor [see, generally, Chan et al., *Hepatocyte Growth Factor-Scatter Factor (HGF-SF) and the C-Met Receptor*, Goldberg and Rosen, eds., Birkhauser Verlag-Basel (1993), pp.67–79]. It has been observed that levels of HGF increase in the plasma of patients with hepatic failure [Gohda et al., supra] and in the plasma [Lindroos et al., *Hepatol.*, 13:734–750 (1991)] or serum [Asami et al., *J. Biochem.*, 109:8–13 (1991)] of animals with experimentally induced liver damage. The kinetics of this response are usually rapid, and precedes the first round of DNA synthesis during liver regeneration. HGF has also been shown to be a mitogen for certain cell types, including melanocytes, renal tubular cells, keratinocytes, certain endothelial cells and cells of epithelial origin [Matsumoto et al., *Biochem. Biophys. Res. Commun.*, 176:45–51 (1991); Igawa et al., *Biochem. Biophys. Res. Commun.*, 174:831–838 (1991); Han et al., *Biochem.*, 30:9768–9780 (1991); Rubin et al., *Proc. Natl. Acad. Sci. USA*, 88:415–419 (1991)]. Both HGF andthe c-Met protooncogene have been postulated to play a role in microglial reactions to CNS injuries [DiRenzo et al., *Oncogene*, 8:219–222 (1993)].

HGF can also act as a "scatter factor", an activity that promotes the dissociation of epithelial and vascular endothelial cells in vitro [Stoker et al., *Nature*, 327:239–242 (1987); Weidner et al., *J. Cell Biol.*, 111:2097–2108 (1990); Naldini et al., *EMBO J.*, 10:2867–2878 (1991); Giordano et al., *Proc. Natl. Acad. Sci. USA*, 90:649–653 (1993)]. Moreover, HGF has recently been described as an epithelial morphogen [Montesano et al., *Cell*, 67:901–908 (1991)]. Therefore, HGF has been postulated to be important in tumor invasion [Comoglio, *Hepatocyte Growth Factor-Scatter Factor (HGF-SF) and the C-Met Receptor*, Goldberg and Rosen, eds., Birkhauser Verlag-Basel (1993), pp.

131–165]. Bellusci et al., *Oncogene,* 9:1091–1099 (1994) report that HGF can promote motility and invasive properties of NBT-II bladder carcinoma cells.

c-Met RNA has been detected in several murine myeloid progenitor tumor cell lines [Iyer et al., *Cell Growth and Differentiation,* 1:87–95 (1990)]. Further, c-Met is expressed in various human solid tumors [Prat et al., *Int., J. Cancer,* supra]. Overexpression of the c-Met oncogene has also been suggested to play a role in the pathogenesis and progression of thyroid tumors derived from follicular epithelium [DiRenzo et al., *Oncogene,* 7:2549–2553 (1992)]. Chronic c-Met/HGF receptor activation has also been observed in certain malignancies [Cooper et al., *EMBO J.,* 1:2623 (1986); Giordano et al., *Nature,* 339:155 (1989)].

In view of the role of HGF and/or c-Met in potentiating or promoting such diseases or pathological conditions, it would be useful to have a means of substantially reducing or inhibiting one or more of the biological effects of HGF and c-Met.

SUMMARY OF THE INVENTION

The invention provides HGF receptor antagonists which are capable of specifically binding to a HGF receptor. Preferred HGF receptor antagonists are capable of substantially reducing or inhibiting the mitogenic, motogenic (migration or scatter) or other biological activity of HGF or HGF receptor activation. and thus are useful in the treatment of various diseases and pathological conditions such as cancer. In one embodiment of the invention, the HGF receptor antagonist is an antibody. Preferably, this antagonist is a monoclonal antibody, and more preferably, is a Fab fragment of a monoclonal antibody.

The invention also provides hybridoma cell lines which produce HGF receptor antagonist monoclonal antibodies.

The invention also provides HGF receptor antagonists that comprise isolated polypeptide comprising the amino acid sequences of FIG. 1A (SEQ ID NO:1) and FIG. 1B (SEQ ID NO:2). The polypeptides consisting of the amino acid sequences of FIG. 1A (SEQ ID NO: 1) and FIG. 1B (SEQ ID NO:2) correspond to the light chain and heavy chain, respectively, of monoclonal antibody 5D5 Fab, described herein.

The invention also provides chimeric molecules comprising HGF receptor antagonist linked or fused to another, heterologous polypeptide or polymer. An example of such a chimeric molecule comprises a HGF receptor antagonist amino acid sequence linked or fused to an albumin sequence or polyethylene glycol ("PEG") sequence.

The invention further provides an isolated nucleic acid molecule encoding HGF receptor antagonist. In one aspect, the nucleic acid molecule is RNA or DNA that encodes a HGF receptor antagonist or is complementary to a nucleic acid sequence encoding such HGF receptor antagonist. and remains stably bound to it under stringent conditions. In one embodiment, the nucleic acid sequences are selected from:

(a) the nucleic acid sequence of FIG. 1A that codes for residue 1 to residue 220 (i.e., nucleotides 1 through 660; SEQ ID NO:3), inclusive;

(b) the nucleic acid sequence of FIG. 1B that codes for residue 1 to residue 230 (i.e., nucleotides 1 through 690; SEQ ID NO:4), inclusive; or (c) a nucleic acid sequence corresponding to the sequence of (a) or (b) within the scope of degeneracy of the genetic code.

The invention also provides a replicable vector comprising the nucleic acid molecule(s) encoding the HGF receptor antagonist operably linked to control sequence(s) recognized by a host cell transfected or transformed with the vector. A host cell comprising the vector or the nucleic acid molecule(s) is also provided. A method of producing HGF receptor antagonist which comprises culturing a host cell comprising the nucleic acid molecule(s) and recovering the protein from the host cell culture is further provided.

The invention also provides pharmaceutical compositions comprising one or more HGF receptor antagonists in a pharmaceutically-acceptable carrier. In one embodiment, the pharmaceutical composition may be included in an article of manufacture or kit.

The invention also provides methods of employing HGF receptor antagonists, including methods of inhibiting HGF receptor activation.

The invention further provides methods for treating cancer comprising administering to a mammal diagnosed as having cancer an effective amount of a HGF receptor antagonist. The HGF receptor antagonist alone may be administered to the mammal, or alternatively, may be administered to the mammal in combination with other therapeutic agents such as anti-cancer agents.

It is believed that the antagonists can be used to block binding of HGF to HGF receptor(s) or substantially prevent HGF receptor activation, thereby treating pathologic conditions associated with binding of HGF to HGF receptor(s) or with the activation of HGF receptor(s).

BRIEF DESCRIPTION OF THE DRAWINGS

FIGS. 1A and 1B show the amino acid sequences (and encoding nucleotides) for the light chain (FIG. 1A) and heavy chain (FIG. 1B), respectively, of monoclonal antibody 5D5 Fab.

FIGS. 14A–14D are graphs comparing the inhibitory effect of recombinant 5D5 Fab and recombinant anti-VEGF Fab (control Fab) on BaF3-hmet.8 cells in a proliferation assay conducted in the presence or absence of heparin.

DETAILED DESCRIPTION OF THE INVENTION

I. Definitions

Figure 2:
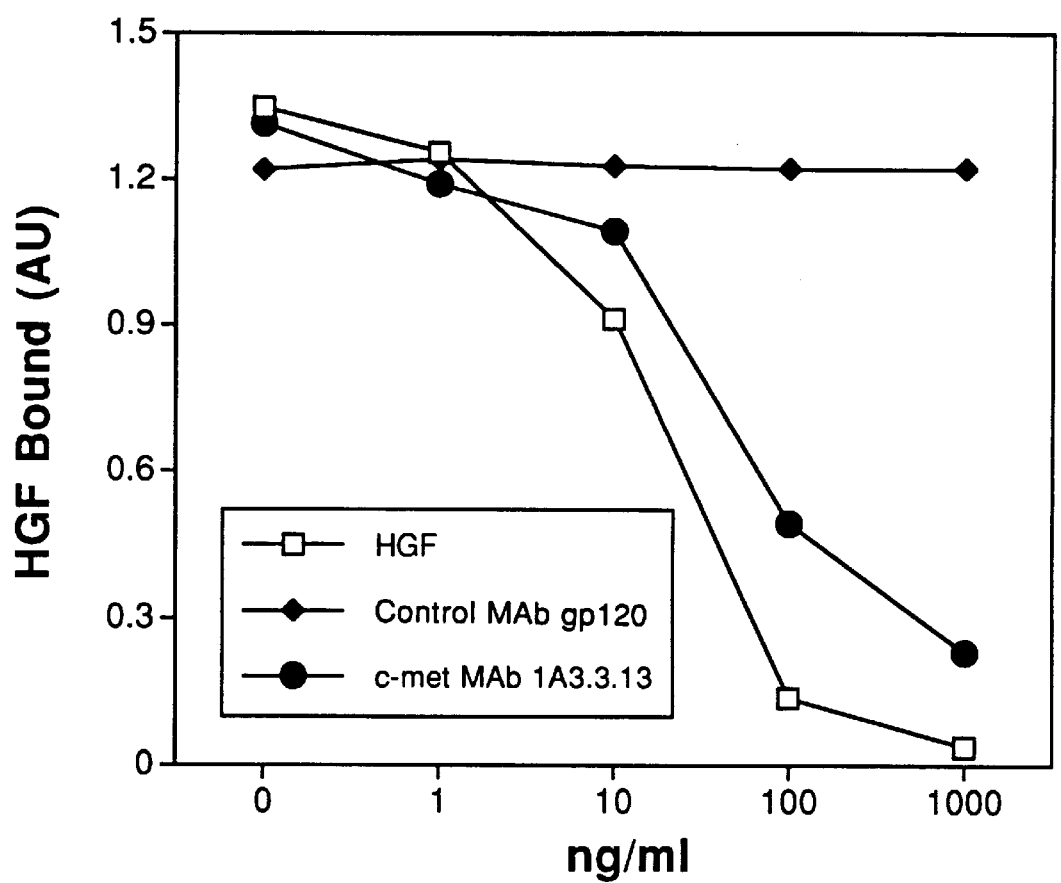
FIG. 2 is a graph showing the inhibition of HGF binding to c-Met-IgG fusion protein by monoclonal antibody 1A3.3.13.

As used herein, the terms "hepatocyte growth factor" and "HGF" refer to a growth factor typically having a structure with six domains (finger, Kringle 1, Kringle 2, Kringle 3, Kringle 4 and serine protease domains) and having the property of binding to a HGF receptor, as defined below. The terms "hepatocyte growth factor" and "HGF" include hepatocyte growth factor from humans ("huHGF") and any non-human mammalian species, and in particular rat HGF. The terms as used herein include mature, pre, pre-pro, and pro forms, purified or isolated from a natural source, chemically synthesized or recombinantly produced. Human HGF is encoded by the cDNA sequence published by Miyazawa et al., 1989, supra, or Nakamura et al., 1989, sunra. The sequences reported by Miyazawa et al. and Nakamura et al. differ in 14 amino acids. The reason for the differences is not entirely clear; polymorphism or cloning artifacts are among the possibilities. Both sequences are specifically encompassed by the foregoing terms. It will be understood that natural allelic variations exist and can occur among individuals, as demonstrated by one or more amino acid differences in the amino acid sequence of each individual. The HGF of the invention preferably has at least about 80% sequence identity, more preferably at least about 90% sequence identity, and even more preferably, at least about 95% sequence identity with a native mammalian HGF. The terms "hepatocyte growth factor" and "HGF" specifically include the delta5 huHGF as disclosed by Seki et al., supra.

The terms "HGF receptor" and "c-Met" when used herein refer to a cellular receptor for HGF, which typically includes an extracellular domain, a transmembrane domain and an intracellular domain, as well as variants and fragments thereof which retain the ability to bind HGF. The terms "HGF receptor" and "c-Met" include the polypeptide molecule that comprises the full-length, native amino acid sequence encoded by the gene variously known as p190$^{MET}$. The present definition specifically encompasses soluble forms of HGF receptor, and HGF receptor from natural sources, synthetically produced in vitro or obtained by genetic manipulation including methods of recombinant DNA technology. The HGF receptor variants or fragments preferably share at least about 65% sequence identity, and more preferably at least about 75% sequence identity with any domain of the human c-Met amino acid sequence published in Rodrigues et al., *Mol. Cell. Biol.*, 11:2962–2970 (1991); Park et al., *Proc. Natl. Acad. Sci.*, 84:6379–6383 (1987); or Ponzetto et al., *Oncogene*, 6:553–559 (1991).

The term "5D5 Fab" is used herein to refer to polypeptide comprising amino acid residues 1 to 220 of the amino acid sequence shown in FIG. 1A (SEQ ID NO: 1) and amino acid residues 1 to 230 of the amino acid sequence shown in FIG. 1B (SEQ ID NO:2), as well as biologically active deletional, insertional, or substitutional variants thereof. In a preferred embodiment, the 5D5 Fab consists of the amino acid sequences shown in FIGS. 1A and 1B, which correspond to the light chain and heavy chain, respectively, of monoclonal antibody 5D5 Fab. In another preferred embodiment, the biologically active variants have at least about 80% sequence identity, more preferably at least about 90% sequence identity, and even more preferably, at least about 95% sequence identity with the sequences described above. The definition encompasses 5D5 Fab obtained from an antibody source, such as papain digestion of monoclonal antibody 5D5 described herein, or prepared by recombinant or synthetic methods, described for instance in Example 13 below.

The term "epitope tagged" when used herein refers to a chimeric polypeptide comprising HGF receptor antagonist, or a portion thereof, fused to a "tag polypeptide". The tag polypeptide has enough residues to provide an epitope against which an antibody can be made, yet is short enough such that it does not interfere with activity of the antagonist. The tag polypeptide preferably also is fairly unique so that the antibody does not substantially cross-react with other epitopes. Suitable tag polypeptides generally have at least six amino acid residues and usually between about 8 to about 50 amino acid residues (preferably, between about 10 to about 20 residues).

As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo half-life of the IgG molecule.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the HGF receptor antagonist natural environment will not be present. Ordinarily, however, isolated polypeptide will be prepared by at least one purification step. Homogeneity here means less than about 5% contamination with other source proteins and polypeptides.

An "isolated" HGF receptor antagonist nucleic acid molecule is a nucleic acid molecule that is identified and separated from at least one contaminant nucleic acid molecule with which it is ordinarily associated in the natural source of the HGF receptor antagonist nucleic acid. An isolated HGF receptor antagonist nucleic acid molecule is other than in the form or setting in which it is found in nature. Isolated HGF receptor antagonist nucleic acid molecules therefore are distinguished from the HGF receptor antagonist nucleic acid molecule as it exists in natural cells. However, an isolated HGF receptor antagonist nucleic acid molecule includes HGF receptor antagonist nucleic acid molecules contained in cells that ordinarily express HGF receptor antagonist where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "amino acid" and "amino acids" refer to all naturally occurring L-α-amino acids. This definition is meant to include norleucine, ornithine, and homocysteine. The amino acids are identified by either the single-letter or three-letter designations:

| Asp | D | aspartic acid | Ile | I | isoleucine |
|-----|---|---------------|-----|---|------------|
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

In the Sequence Listing and Figures, certain other single-letter or three-letter designations are employed to refer to and identify two or more amino acids at a given position in the amino acid sequence. For instance, at amino acid residue 1 in SEQ ID NO:2, the three-letter designation "Glx" is employed to identify that at residue 1, the amino acid may be a glutamine or a glutamic acid residue.

Nucleotide bases referred to in the Sequence Listing and Figures include "A" (adenine), "C" (cytosine), "G" (guanine), "T" (thymine) and "S" (cytosine or guanine).

The term "heparin" is used in a broad sense and refers to a heterogeneous group of sulfated, straight-chain anionic mucopolysaccharides, often referred to as glycosaminoglycans. Although others may be present, the main sugars in heparin are: α-L-iduronic acid 2-sulfate, 2-deoxy-2-sulfamino-α-glucose 6-sulfate, β-glucuronic acid, 2-acetamido-2-deoxy-α-D-glucose, and L-iduronic acid. These and optionally other sugars are typically joined by glycosidic linkages. The molecular weight of heparin typically varies from about 6,000 to about 20,000 Da depending on the source and the method of molecular weight determination. Heparin is a native constituent of various cells and tissues, especially liver and lung, in several mammalian species.

The term "heparin-independent" when used herein describes HGF receptor antagonists which have substantially reduced ability to bind heparin or are unable to bind heparin, or heparin-like glycosaminoglycans, including heparan sulfate and proteoglycans. Determination of whether a HGF receptor antagonist is heparin-independent can be determined by the skilled artisan without undue experimentation. Heparin-independence can be determined, for example, by assaying the antagonist for HGF blocking activity in the presence of heparin, as described in the Examples, and observing the activity of the molecule.

The terms "agonist" and "agonistic" when used herein refer to or describe a molecule which is capable of, directly or indirectly, substantially inducing, promoting or enhancing HGF biological activity or HGF receptor activation.

The terms "antagonist" and "antagonistic" when used herein refer to or describe a molecule which is capable of, directly or indirectly, substantially counteracting, reducing or inhibiting HGF biological activity or HGF receptor activation.

The term "HGF biological activity" when used herein refers to any mitogenic, motogenic or morphogenic activities of HGF or any activities occurring as a result of HGF binding to a HGF receptor. The term "HGF receptor activation" refers to HGF receptor dimerization or HGF receptor-induced tyrosine kinase activity. HGF receptor activation may occur as a result of HGF binding to a HGF receptor, but may alternatively occur independent of any HGF binding to a HGF receptor. HGF biological activity may, for example, be determined in an in vitro or in vivo assay of hepatocyte growth promotion. Adult rat hepatocytes in primary culture have been used to test the effect of HGF on hepatocyte proliferation. Accordingly, the effect of a HGF receptor antagonist can be determined in an assay suitable for testing the ability of HGF to induce DNA synthesis of rat hepatocytes in primary cultures. Human hepatocytes can be cultured similarly to the methods established for preparing primary cultures of normal rat hepatocytes. Alternatively, the effect of a HGF receptor antagonist can be determined in an assay suitable for testing the ability of HGF to induce DNA synthesis in other types of cells expressing HGF receptor(s), such as mink lung cells or human mammary epithelial cells described in Examples 4 and 5. DNA synthesis can, for example, be assayed by measuring incorporation of $^3$H-thymidine into DNA. The effectiveness of the HGF receptor antagonist can be determined by its ability to block proliferation and incorporation of the $^3$H-thymidine into DNA. The effect of HGF receptor antagonists can also be tested in vivo in animal models.

The term "antibody" is used herein in a broad sense and includes intact immunoglobulin or antibody molecules, polyclonal antibodies, multispecific antibodies (i.e., bispecific antibodies formed from at least two intact antibodies) and immunoglobulin fragments (such as Fab, F(ab')$_2$, or Fv), so long as they exhibit any of the desired antagonistic properties described herein. Antibodies are typically proteins or polypeptides which exhibit binding specificity to a specific antigen. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains [Chothia et al., *J. Mol. Biol.*, 186:651–663 (1985);

Novotny and Haber, *Proc. Natl. Acad. Sci. USA,* 82:4592–4596 (1985)]. The light chains of antibodies from any vertebrate species can be assigned to one of two clearly distinct types, called kappa (κ) and lambda (λ), based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG and IgM. and several of these may be further divided into subclasses (isotypes), e.g., IgG-1, IgG-2, IgG-3, and IgG4; IgA-1 and IgA-2. The heavy chain constant domains that correspond to the different classes of immunoglobulins are called α, delta, epsilon, γ, and μ, respectively.

"Antibody fragments" comprise a portion of an intact antibody, generally the antigen binding or variable region of the intact antibody. Examples of antibody fragments include Fab, Fab', F(ab')2, and Fv fragments, diabodies, single chain antibody molecules, and multispecific antibodies formed from antibody fragments.

The term "variable" is used herein to describe certain portions of the variable domains which differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions. largely adopting a β-sheet configuration. connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies [see Kabat, E. A. et al., *Sequences of Proteins of Immunological Interest*, National Institutes of Health, Bethesda, Md. (1987)]. The constant domains are not involved directly in binding an antibody to an antigen, but exhibit various effector functions, such as participation of the antibody in antibody-dependent cellular toxicity.

The term "monoclonal antibody" as used herein refers to an antibody obtained from a substantially homogeneous population of antibodies, i.e., the individual antibodies comprising the population are identical except for possible naturally occurring mutations that may be present in minor amounts. The monoclonal antibodies herein specifically include "chimneric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity [U.S. Pat. No. 4,816,567; Morrison et al., *Proc. Natl. Acad. Sci. USA,* 81:6851–6855 (1984)]. The terms "cancer" and "cancerous" when used herein refer to or describe the physiological condition in mammals that is typically characterized by unregulated cell growth. Examples of cancer include but are not limited to, carcinoma, lymphoma, sarcoma, blastoma and leukemia. More particular examples of such cancers include squamous cell carcinoma, lung cancer (small cell and non-small cell), gastrointestinal cancer, liver cancer, kidney cancer, pancreatic cancer, cervical cancer, bladder cancer. hepatoma, breast cancer, colon carcinoma, and head and neck cancer. While the term "cancer" as used herein is not limited to any one specific form of the disease, it is believed that the methods of the invention will be particularly effective for cancers which are found to be accompanied by increased levels of HGF or overexpression or activation of HGF receptor in the mammal.

The terms "treating," "treatment," and "therapy" as used herein refer to curative therapy, prophylactic therapy, and preventative therapy.

The term "mammal" as used herein refers to any animal classified as a mammal, including humans, cows, horses, dogs and cats. In a preferred embodiment of the invention, the mammal is a human.

II. Compositions and Methods of the Invention

In one embodiment of the invention, HGF receptor antagonists are provided. Non-limiting examples of HGF receptor antagonists include antibodies, polypeptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like.

A. Antibody Compositions

In one embodiment of invention, the HGF receptor antagonists of the invention comprise HGF receptor antibodies. For instance, the antagonist antibodies may be polyclonal antibodies. Methods of preparing polyclonal antibodies are known to the skilled artisan. Polyclonal antibodies can be raised in a mammal, for example, by one or more injections of an immunizing agent and, if desired. an adjuvant. Typically, the immunizing agent and/or adjuvant will be injected in the mammal by multiple subcutaneous or intraperitoneal injections. Preferably, the immunizing agent includes the c-Met polypeptide or a fusion protein thereof. It may be useful to conjugate the immunizing agent to a protein known to be immunogenic in the mammal being immunized. Examples of such immunogenic proteins which may be employed include but are not limited to keyhole limpet hemocyanin, serum albumin, bovine thyroglobulin, and soybean uypsin inhibitor. An aggregating agent such as alum may also be employed to enhance the mammal's immune response. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation. The mammal can then be bled, and the serum assayed for HGF receptor antibody titer. If desired, the mammal can be boosted until the antibody titer increases or plateaus.

The antagonist antibodies of the invention may, alternatively, be monoclonal antibodies. Antagonist monoclonal antibodies of the invention may be prepared using hybridoma methods, such as those described by Kohler and Milstein, *Nature,* 256:495 (1975). In a hybridoma method, a mouse or other appropriate host animal, is typically immunized (such as described above) with an immunizing agent to elicit lymphocytes that produce or are capable of producing antibodies that will specifically bind to the immunizing agent. Alternatively, the lymphocytes may be immunized in vitro.

Preferably, the immunizing agent includes the c-Met polypeptide or a fusion protein thereof. The immunizing agent may alternatively comprise a fragment or portion of HGF or a HGF receptor having one or more amino acid residues that participate in the binding of HGF to its receptor. In a more preferred embodiment, the immunizing agent comprises an extracellular domain of c-Met fused to an IgG sequence. such as described in Example 1.

Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Princinles and Practice,* Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance. from the Salk Institute Cell Distribution Center, San Diego, Calif. and the American Type Culture Collection, Rockville, Md. An example of such a murine myeloma cell line is P3X63AgU. 1, described in Example 1 below. Human myeloma and mouse-human heteromyeloma cell lines also have been described for the production of human monoclonal antibodies [Kozbor, *J. Immunol.,* 133:3001–3005 (1984): Brodeur et al., *Monoclonal Antibody Production Techniques and Applications,* Marcel Dekker, Inc., New York, (1987) pp. 51–63].

The culture medium in which the hybridoma cells are cultured can then be assayed for the presence of monoclonal antibodies directed against a HGF receptor. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art, and are described further in the Examples below. The binding affinity of the monoclonal antibody can, for example, be determined by the Scatchard analysis of Munson and Pollard, *Anal. Biochem.,* 107:220–239 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as. for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4.816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, *E. coli,* Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra]) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chirneric bivalent antibody comprising one antigen-combining site having specificity for a HGF receptor and another antigen-combining site having specificity for a different antigen, such as HER2 or CD3.

It is believed, however, that monovalent antibodies capable of binding to a HGF receptor will be especially useful as HGF receptor antagonists. While not being bound to any particular theory, it is presently believed that activation of c-Met may proceed by a mechanism wherein huHGF binding to c-Met induces aggregation or dimerization of the receptors which in turn activates intracellular receptor kinase activity. Because monovalent antibodies will likely be unable to induce such aggregation or dimerization, the monovalent antibodies should not activate c-Met. Such monovalent antibodies may be directed against the HGF binding site of the receptor or may otherwise be capable of interfering with HGF, its fragments or its variants binding to the HGF receptor, such as by sterically hindering HGF, its fragments or its variants access to the receptor. Alternatively, the monovalent antibodies may be capable of sterically preventing HGF receptor dimerization.

Methods for preparing monovalent antibodies are well known in the art. For example. one method involves recombinant expression of immunoglobulin light chain and modified heavy chain. The heavy chain is truncated generally at any point so as to prevent heavy chain crosslinking. Alternatively, the relevant cysteine residues may be substituted with another amino acid residue or are deleted so as to prevent crosslinking. Recombinant expression of Fab light chain and heavy chain is described in further detail below.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published 12/22/94 and U.S. Pat. No. 4,342,566. Papain digestion is also described in Examples 6 and 7 below. Papain digestion of antibodies typically produces two identical antigen binding fragments, called Fab fragments, each with a single antigen binding site, and a residual Fc fragment. Pepsin treatment yields an F(ab')$_2$ fragment that has two antigen combining sites and is still capable of cross-linking antigen.

The Fab fragments produced in the antibody digestion also contain the constant domains of the light chain and the first constant domain (CH$_1$) of the heavy chain. Fab' fragments differ from Fab fragments by the addition of a few residues at the carboxy terminus of the heavy chain CH$_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

In a preferred embodiment of the invention, the antagonists comprise Fab fragments of monoclonal antibodies specific for c-Met. In a more preferred embodiment, the monoclonal antibody Fab fragments have the same biological characteristics as the monoclonal antibody Fab fragments produced by digesting either of the monoclonal antibodies secreted by the hybridoma cell lines deposited under American Type Culture Collection Accession Nos. ATCC HB-11894 or ATCC HB-11895. The term "biological characteristics" is used to refer to the in vitro and/or in vivo activities of the monoclonal antibody, e.g., ability to substantially reduce or inhibit binding of huHGF to c-Met or to substantially reduce or inhibit c-Met activation. Accordingly, the monovalent antibody preferably binds to substantially the same epitope as the 1A3.3.13 antibody or the 5D5.1 1.6 antibody disclosed herein. This can be determined by conducting assays described herein and in the Examples. For instance, to determine whether a monoclonal antibody has the same specificity as the 1A3.3.13 antibody specifically disclosed (i.e., the antibody having the ATCC deposit No. HB-11894) or the 5D5.11.6 antibody specifically disclosed (i.e., the antibody having the ATCC deposit No. HB-11895), one can use a competitive ELISA binding assay such as those described in the Examples. In an even more preferred embodiment, the monoclonal antibody Fab fragments are heparin-independent antagonists, as defined herein. In a preferred embodiment of the invention, the monoclonal antibody or fragment thereof will inhibit the binding of HGF, its fragments or its variants, or the mitogenic activity of HGF, its fragments, or its variants at least about 50%, preferably, greater than about 80%, and more preferably, greater than about 90%, as determined by an in vitro competitive binding assay or proliferation assay, such as described in the Examples below.

In addition to the antagonist antibodies described above. it is contemplated that chimeric or hybrid antagonist antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

The antagonist antibodies of the invention may also comprise diabodies. The term "diabodies" refers to small antibody fragments with two antigen binding sites, which fragments comprise a heavy chain variable domain (V$_H$) connected to a light chain variable domain (V$_L$) in the same polypeptide chain (V$_H$-V$_L$). By using a linker that is too short to allow pairing between the two domains on the same chain, the domains are forced to pair with the complementary domains of another chain and create two antigen binding sites. Diabodies are described in further detail, for example, in EP404,097; WO 93/11161; and Hollinger et al., *Proc. Natl. Acad. Sci*, 90:6444–6448 (1993).

The antagonist antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general. the humanized antibody will comprise substantially all of at least one, and typically two, variable domains, in which all or substantially all of the CDR regions correspond to those of a non-human immunoglobulin and all or substantially all of the FR regions are those of a human inmuunoglobulin consensus sequence. The humanized antibody optimally also will comprise at least a portion of an immunoglobulin constant region (Fc), typically that of a human immunoglobulin [Jones et al., *Nature*, 321:522–525 (1986); Reichmann et al., *Nature*, 332:323–327 (1988); and Presta, *Curr. Op. Struct. Biol*, 2,:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody [Sims et al.,*J. lmmunol.,* 151:2296 (1993); Chothia and Lesk, *J. Mol. Biol.,* 196:901 (1987)]. Another method uses a particular framework derived from the consensus sequence of all human antibodies of a particular subgroup of light or heavy chains. The same framework may be used for several different humanized antibodies [Carter et al., *Proc. Natl. Acad. Sci. USA,* 89:4285 (1992); Presta et al., *J. Immunol.,* 151:2623–2632 (1993)].

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding [see, WO 94/04679 published 3 Mar. 1994].

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge [see, e.g., Jakobovits et al., *Proc. Natl. Acad. Sci. USA*, 90:2551–255 (1993); Jakobovits et al., *Nature*, 362:255–258 (1993); Bruggermann et al., *Year in Immuno.*, 7:33 (1993)]. Human antibodies can also be produced in phage display libraries [Hoogenboom and Winter, *J. Mol. Biol.*, 222:381 (1991); Marks et al., *J. Mol. Biol.*, 222:581 (1991)]. The techniques of Cote et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86–95 (1991)].

B. Polypeptides and Nucleic Acid Compositions

The present invention also provides HGF receptor antagonists comprising one or more isolated polypeptides. In one embodiment, the antagonist comprises residues 1 to 220 of the amino acid sequence shown in FIG. 1A (SEQ ID NO:1) and residues 1 to 230 of the amino acid sequence shown in FIG. 1B (SEQ ID NO:2). Preferably, the antagonist comprises two isolated polypeptides which correspond to the light chain and heavy chain, respectively, of an anti-HGF receptor monoclonal antibody Fab.

1. Preparation of HGF Receptor Antagonist

The description below relates primarily to production of the HGF receptor antagonist by culturing cells transformed or transfected with a vector containing the antagonist nucleic acid and recovering the polypeptide(s) from the cell culture. It is of course, contemplated that alternative methods, which are well known in the art, may be employed to prepare the HGF receptor antagonist polypeptide.

1. Isolation of DNA Encoding HGF Receptor Antagonist

The DNA encoding the HGF receptor antagonist may be obtained from any cDNA library prepared from tissue believed to possess the antagonist mRNA and to express it at a detectable level. Accordingly, human c-Met antagonist DNA can be conveniently obtained from a cDNA library prepared from human tissues. The c-Met antagonist-encoding gene may also be obtained from a genomic library or by oligonucleotide synthesis.

Libraries can be screened with probes (such as antibodies to the c-Met receptor antagonist or oligonucleotides of at least about 20–80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding the receptor antagonist is to use PCR methodology [Sambrook et al., supra; Dieffenbach et al., *PCR Primer:A Laboratory Manual* (Cold Spring Harbor Laboratory Press, 1995)].

One method of screening employs selected oligonucleotide sequences to screen cDNA libraries from various human tissues. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling.

Nucleic acid having all the protein coding sequence may be obtained by screening selected cDNA or genomic libraries using the amino acid sequence disclosed herein, and, if necessary, using conventional primer extension procedures as described in Sambrook et al., supra, to detect precursors and processing intermediates of mRNA that may not have been reverse-transcribed into cDNA.

Amino acid sequence variants of the antagonist polypeptide can be prepared by introducing appropriate nucleotide changes into its DNA, or by synthesis of the desired antagonist polypeptide. Such variants represent insertions, substitutions, and/or deletions of residues within or at one or both of the ends of the amino acid sequences shown in FIGS. 1A and 1B for the 5D5 Fab. Any combination of insertion, substitution, and/or deletion can be made to arrive at the final construct, provided that the final construct possesses the desired antagonistic activity as defined herein. In a preferred embodiment, the variants have at least about 80% sequence identity, more preferably, at least about 90% sequence identity, and even more preferably, at least about 95% sequence identity with the sequences identified herein for the 5D5 Fab.

Variations in the native sequence as described above can be made using any of the techniques and guidelines for conservative and non-conservative mutations set forth in U.S. Pat. No. 5,364,934. These include oligonucleotide-mediated (site-directed) mutagenesis, alanine scanning, and PCR mutagenesis.

2. Insertion of Nucleic Acid into A Replicable Vector

The nucleic acid (e.g., cDNA or genomic DNA) encoding the receptor antagonist may be inserted into a replicable vector for further cloning (amplification of the DNA) or for expression. Various vectors are publicly available. The vector components generally include, but are not limited to, one or more of the following: a signal sequence, an origin of replication, one or more marker genes, an enhancer element, a promoter, and a transcription termination sequence, each of which is described below.

(i) Signal Sequence Component

The HGF receptor antagonist may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the antagonist DNA that is inserted into the vector. The heterologous signal sequence selected preferably is one that is recognized and processed (i.e., cleaved by a signal peptidase) by the host cell. The signal sequence may be a prokaryotic signal sequence selected, for example, from the group of the alkaline phosphatase, penicillinase, 1pp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species. as well as viral secretory leaders, for example, the herpes simplex glycoprotein D signal.

The DNA for such precursor region is preferably ligated in reading frame to DNA encoding the antagonist.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 $\mu$ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used because it contains the early promoter).

Most expression vectors are "shuttle" vectors, i.e., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of the receptor antagonist DNA. However, the recovery of genomic DNA encoding the antagonist is more complex than that of an exogenously replicated vector because restriction enzyme digestion is required to excise the antagonist DNA.

(iii) Selection Gene Component

Expression and cloning vectors typically contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin [Southern et al., *J. Molec. Appl. Genet.*, 1:327 [1982]), mycophenolic acid (Mulligan et al., *Science*, 209:1422 (1980)] or hygromycin [Sugden et al., *Mol. Cell. Biol.*, 5:410–413 (1985)]. The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the antagonist nucleic acid. such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the receptor antagonist. Amplification is the process by which genes in greater demand for the production of a protein critical for growth are reiterated in tandem within the chromosomes of successive generations of recombinant cells. Other examples of amplifiable genes include metallothionein-I and -II, adenosine deaminase, and ornithine decarboxylase.

Cells transformed with the DHFR selection gene may first be identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub et al., *Proc. Natl. Acad. Sci. USA*, 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding the receptor antagonist. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells (particularly wild-type hosts that contain endogenous DHFR) transformed or co-transformed with DNA sequences encoding HGF receptor antagonist, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp 1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No.44076 or PEP4-1 [Jones, *Genetics*, 85:12 (1977)]. The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 $\mu$m circular plasmid pKD1 can be used for transformation of Kluyveromyces yeasts (Bianchi et al., *Curr. Genet.*, 12:185 (1987)]. More recently, an expression system for large-scale production of recombinant calf chymosin was reported for *K. lactis* [Van den Berg, *Bio/Technology* 8:135 (1990)]. Stable multicopy expression vectors for secretion of mature recombinant human serum albumin by industrial strains of Kluyveromyces have also been disclosed [Fleer et al., *Bio/Technology*, 9:968–975 (1991)].

(iv) Promoter Component

Expression and cloning vectors usually contain a promoter that is recognized by the host organism and is operably linked to the receptor antagonist nucleic acid sequence. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to receptor antagonist encoding DNA by removing the promoter from the source DNA by restriction enzyme digestion and inserting the isolated promoter sequence into the vector. Various heterologous promoters may be used to direct amplification and/or expression of the receptor antagonist DNA.

Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21–25 (1983)]. However, other known bacterial promoters are suitable. Their nucleotide sequences have been published, thereby enabling a skilled worker operably to ligate them to DNA encoding receptor antagonist [Siebenlist et al., *Cell*, 20:269 (1980)] using linkers or adaptors to supply any required restriction sites. Promoters for use in bacterial systems also will contain a Shine-Dalgarno (S.D.) sequence operably linked to the DNA encoding HGF receptor antagonist.

Promoter sequences are known for eukaryotes. Virtually all eukaryotic genes have an AT-rich region located approximately 25 to 30 bases upstream from the site where transcription is initiated. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase [Hitzeman et al., *J.Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

HGF receptor antagonist transcription from vectors in mammalian host cells is controlled, for example, by promoters obtained from the genomes of viruses such as polyoma virus, fowipox virus (UK 2,211,504 published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), or from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication [Fiers et al., *Nature*, 273:113 (1978); Mulligan and Berg, *Science*, 209:1422–1427 (1980); Pavlakis et al., *Proc. Natl. Acad. Sci. USA*, 78:7398–7402 (1981)]. The immediate early promoter of the human cytomegalovirus is conveniently obtained as a HindIII E restriction fragment [Greenaway et al., *Gene*, 18:355–360 (1982)]. A system for expressing DNA in mammalian hosts using the bovine papilloma virus as a vector is disclosed in U.S. Pat. No. 4,419,446. A modification of this system is described in U.S. Pat. No. 4,601,978 [See also Gray et al., *Nature*, 295:503–508 (1982) on expressing cDNA encoding immune interferon in monkey cells; Reyes et al., *Nature*, 297:598–601 (1982) on expression of human β-interferon cDNA in mouse cells under the control of a thymidine kinase promoter from herpes simplex virus; Canaani and Berg, *Proc. Natl. Acad. Sci. USA* 79:5166–5170 (1982) on expression of the human interferon β1 gene in cultured mouse and rabbit cells; and Gorman et al., *Proc. Nati. Acad. Sci. USA*, 79:6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter).

(v) Enhancer Element Component

Transcription of a DNA encoding the HGF receptor antagonist of this invention by higher eukaryotes may be increased by inserting an enhancer sequence into the vector. Enhancers are cis-acting elements of DNA, usually about from 10 to 300 bp, that act on a promoter to increase its transcription. Enhancers are relatively orientation and position independent, having been found 5' [Laimins et al., *Proc. Natl. Acad. Sci. USA*, 78:993 (1981]) and 3' [Lusky et al., *Mol. Cell Bio.*, 3:1108 (1983]) to the transcription unit, within an intron (Banerji et al., *Cell*, 33:729 (1983)], as well as within the coding sequence itself [Osborne et al., *Mol. Cell Bio.*, 4:1293 (1984)]. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature*, 297:17–18 (1982) on enhancing elements for activation of eukaryotic promoters. The enhancer may be spliced into the vector at a position 5' or 3' to the HGF receptor antagonist-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding HGF receptor antagonist.

(vii) Construction and Analysis of Vectors

Construction of suitable vectors containing one or more of the above-listed components employs standard ligation techniques. Isolated plasmids or DNA fragments are cleaved, tailored, and re-ligated in the form desired to generate the plasmids required.

For analysis to conftrm correct sequences in plasmids constructed, the ligation mixtures can be used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.,* 9:309 (1981) or by the method of Maxam et al., *Methods in Enzymology,* 6:499 (1980).

(viii) Transient Expression Vectors

Expression vectors that provide for the transient expression in mammalian cells of DNA encoding HGF receptor antagonist may be employed. In general, transient expression involves the use of an expression vector that is able to replicate efficiently in a host cell, such that the host cell accumulates many copies of the expression vector and, in turn, synthesizes high levels of a desired polypeptide encoded by the expression vector [Sambrook et al., supra]. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of the receptor antagonists.

(ix) Suitable Exemplarv Vertebrate Cell Vectors

Other methods, vectors, and host cells suitable for adaptation to the synthesis of HGF receptor antagonist in recombinant vertebrate cell culture are described in Gething et al., *Nature,* 293:620–625 (1981); Mantei et al., *Nature,* 281:40–46 (1979); EP 117,060; and EP 117,058.

3. Selection and Transformation of Host Cells

Suitable host cells for cloning or expressing the DNA in the vectors herein are the prokaryote, yeast, or higher eukaryote cells described above. Suitable prokaryotes for this purpose include but are not limited to eubacteria, such as Gram-negative or Gram-positive organisms, for example, Enterobacteriaceae such as Escherichia, e.g., *E. coli,* Enterobacter, Erwinia, Klebsiella, Proteus, Salmonella. e.g., *Salmonella typhimurium,* Serratia, e.g., *Serratia marcescans,* and Shigella, as well as Bacilli such as *B. subtilis* and *B. licheniformis* (e.g., *B. licheniformis* 41 P disclosed in DD 266.710 published 12 Apr. 1989), Pseudomonas such as *P. aeruginosa,* and Streptomyces. Preferably, the host cell should secrete minimal amounts of proteolytic enzymes.

In addition to prokaryotes, eukaryotic microbes such as filamentous fungi or yeast are suitable cloning or expression hosts for HGF receptor antagonist-encoding vectors. *Saccharomyces cerevisiae,* or common baker's yeast, is the most commonly used among lower eukaryotic host microorganisms. However, a number of other genera, species, and strains are commonly available and useful herein.

Suitable host cells for the expression of glycosylated HGF receptor antagonist are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified [See, e.g., Luckow et al., *Bio/Technology,* 6:47–55 (1988); Miller et al.. in *Genetic Engineering, Setlow et al., eds., Vol.* 8 (Plenum Publishing, 1986), pp. 277–279; and Maeda et al., *Nature,* 315:592–594 (1985)]. A variety of viral strains for transfection are publicly available, e.g., the L-1 variant of *Autographa californica* NPV and the Bm-5 strain of *Bombyx mori* NPV.

Plant cell cultures of cotton, corn, potato, soybean, petunia tomato, and tobacco can be utilized as hosts. Typically, plant cells are transfected by incubation with certain strains of the bacterium *Agrobacterium tumefaciens,* which has been previously manipulated to contain the receptor antagonist-encoding DNA. During incubation of the plant cell culture with *A. tumefaciens,* the DNA encoding the receptor antagonist is transferred to the plant cell host such that it is transfected, and will, under appropriate conditions, express the receptor antagonist-encoding DNA. In addition, regulatory and signal sequences compatible with plant cells are available, such as the nopaline synthase promoter and polyadenylation signal sequences [Depicker et al., *J. Mol. Appl. Gen.,* 1:561 (1982)]. In addition, DNA segments isolated from the upstream region of the T-DNA 780 gene are capable of activating or increasing transcription levels of plant-expressible genes in recombinant DNA-containing plant tissue [EP 321,196 published 21 Jun. 1989].

Propagation of vertebrate cells in culture (tissue culture) is also well known in the art [See, e.g., *Tissue Culture,* Academic Press, Kruse and Patterson, editors (1973)]. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.,* 36:59 (1977)); baby hamster kidney cells (BHK, ATCC CCL 10); Chinese hamster ovary cells/-DHFR (CHO, Urlaub and Chasin, *Proc. Natl. Acad. Sci. USA,* 77:4216 (1980)); mouse sertoli cells (TM4, Mather, *Biol. Reprod.,* 2:243–35 251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK. ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.,* 383:44–68 (1982)); MRC 5 cells; and FS4 cells.

Host cells are transfected and preferably transformed with the above-described expression or cloning vectors for HGF receptor antagonist production and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable. either as an extrachromosomal element or by chromosomal integrant. Depending on the host cell used, transformation is done using standard techniques appropriate to such cells. The calcium treatment employing calcium chloride. as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published 29 Jun. 1989. In addition, plants may be transfected using ultrasound treatment as described in WO 91/00358 published 10 Jan. 1991.

For mammalian cells without such cell walls, the calcium phosphate precipitation method of Graham and van der Eb, *Virology*, 51:456–457 (1978) is preferred. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyomithine, may also be used. For various techniques for transforming mammalian cells, see Keown et al., *Methods in Enzymology*, 18:527–537 (1990) and Mansour et al., *Nature*, 336:348–352 (1988).

4. Culturing the Host Cells

Prokaryotic cells used to produce HGF receptor antagonist may be cultured in suitable media as described generally in Sambrook et al., supra.

The mammalian host cells used to produce HGF receptor antagonist may be cultured in a variety of media. Examples of commercially available media include Ham's F1O (Sigma), Minimal Essential Medium ("MEM", Sigma), RPMI-1640 (Sigma), and Dulbecco's Modified Eagle's Medium ("DMEM", Sigma). Any such media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at ftnal concentrations in the micromolar range), and glucose or an equivalent energy source. Any other necessary supplements may also be included at appropriate concentrations that would be known to those skilled in the art. The culture conditions. such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: a Practical Approach*, M. Butler, ed. (IRL Press, 1991).

The host cells referred to in this disclosure encompass cells in culture as well as cells that are within a host animal.

5. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201–5205 (1980)], dot blotting (DNA analysis), or in situ hybridization, using an appropriately labeled probe, based on the sequences provided herein. Various labels may be employed, most commonly radioisotopes, and particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionucleotides, fluorescers or enzymes. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. With immunohistochemical staining techniques, a cell sample is prepared. typically by dehydration and fixation, followed by reaction with labeled antibodies specific for the gene product coupled, where the labels are usually visually detectable, such as enzymatic labels, fluorescent labels, or luminescent labels. Antibodies useful for immunohistochemical staining and/or assay of sample fluids may be either monoclonal or polyclonal, and may be prepared in any mammal.

6. Purification of HGF Receptor Antagonist Polvpeltide

HGF receptor antagonist preferably is recovered from the culture medium as a secreted polypeptide, although it also may be recovered from host cell lysates when directly produced without a secretory signal. If the receptor antagonist is membrane-bound, it can be released from the membrane using a suitable detergent solution (e.g. Triton-X 100) or its extracellular region may be released by enzymatic cleavage.

When the antagonist is produced in a recombinant cell other than one of human origin, the antagonist polypeptide is free of proteins or polypeptides of human origin. However, it may be desired to purify the receptor antagonist from recombinant cell proteins or polypeptides to obtain preparations that are substantially homogeneous as to the receptor antagonist. As a first step, the culture medium or lysate may be centrifuged to remove particulate cell debris. HGF receptor antagonist thereafter is purified from contaminant soluble proteins and polypeptides, with the following procedures being exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; and protein A Sepharose columns to remove contaminants such as IgG.

A protease inhibitor such as phenyl methyl sulfonyl fluoride (PMSF) also may be useful to inhibit proteolytic degradation during purification, and antibiotics may be included to prevent the growth of adventitious contaminants.

7. Covalent Modifications

Covalent modifications of HGF receptor antagonists are included within the scope of this invention. One type of covalent modification of the HGF receptor antagonist is introduced into the molecule by reacting targeted amino acid residues of the antagonist with an organic derivatizing agent that is capable of reacting with selected side chains or the N- or C- terminal residues of the antagonist.

Derivatization with bifunctional agents is useful for crosslinking the antagonist to a water-insoluble support matrix or surface for use in a method for purifying. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photo-activatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the a-amino groups of lysine, arginine, and histidine side chains [T. E. Creighton, *Proteins: Structure and Molecular Properties*, W. H. Freeman & Co., San Francisco, pp. 79–86 (1983)], acetylation of the N-terminal amine, and amidation of any C-terminal carboxyl group. The modified forms of the residues fall within the scope of the present invention.

Another type of covalent modification of the receptor antagonist polypeptide included within the scope of this invention comprises altering the native glycosylation pattern of the polypeptide. "Altering the native glycosylation pattern" is intended for purposes herein to mean deleting one or more carbohydrate moieties and/or adding one or more glycosylation sites that are not present in the native polypeptide.

Glycosylation of polypeptides is typically either N-linked or O-linked. N-linked refers to the attachment of the carbohydrate moiety to the side chain of an asparagine residue. The tripeptide sequences asparagine-Z-serine and asparagine-Z-threonine, where Z is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxylamino acid, most commonly serine or threonine, although 5-hydroxyproline or 5-hydroxylysine may also be used.

Addition of glycosylation sites to the polypeptide may be accomplished by altering the amino acid sequence such that it contains one or more of the above-described tripeptide sequences (for N-linked glycosylation sites). The alteration may also be made by the addition of, or substitution by, one or more serine or threonine residues to the native sequence (for O-linked glycosylation sites). The amino acid sequence may optionally be altered through changes at the DNA level, particularly by mutating the DNA encoding the polypeptide at preselected bases such that codons are generated that will translate into the desired amino acids. The DNA mutation(s) may be made using methods described above and in U.S. Pat. No. 5,364.934, supra.

Another means of increasing the number of carbohydrate moieties on the polypeptide is by chemical or enzymatic coupling of glycosides to the polypeptide. Depending on the coupling mode used. the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston, *CRC Crit. Rev. Biochem.*, pp. 259–306 (1981).

Removal of carbohydrate moieties present on the polypeptide may be accomplished chemically or enzymatically or by mutational substitution of codons encoding for amino acid residues that serve as targets for glycosylation. For instance, chemical deglycosylation by exposing the polypeptide to the compound trifluoromethanesulfonic acid, or an equivalent compound can result in the cleavage of most or all sugars except the linking sugar (N-acetylglucosamine or N-acetylgalactosamine), while leaving the polypeptide intact. Chemical deglycosylation is described by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Glycosylation at potential glycosylation sites may be prevented by the use of the compound tunicamycin as described by Duskin et al., *J. Biol. Chem.*, 257:3105 (1982). Tunicamycin blocks the formation of protein-N-glycoside linkages.

Another type of covalent modification comprises linking the HGF receptor antagonist to one of a variety of nonproteinaceous polymers, e.g., polyethylene glycol ("PEG"), polypropylene glycol, or polyoxyalkylenes, in the manner set forth in U.S. Pat. Nos. 4,640,835; 4,496,689; 4,301,144; 4,670,417; 4,791,192 or 4,179,337. WO 93/00109 also describes methods of linking amino acid residues in polypeptides to PEG molecules.

8. HGF Receptor Antagonist Chimeras

The present invention also provides chimeric molecules comprising HGF receptor antagonist fused to another, heterologous polypeptide.

In one embodiment, the chimeric molecule comprises a fusion of the antagonist with a tag polypeptide which provides an epitope to which an anti-tag antibody can selectively bind. The epitope tag is generally placed at the amino- or carboxyl- terminus of the antagonist. The presence of such epitope-tagged forms of the antagonist can be detected using an antibody against the tag polypeptide. Also, provision of the epitope tag enables the antagonist to be readily purified by affinity purification using an anti-tag antibody or another type of affinity matrix that binds to the epitope tag.

Various tag polypeptides and their respective antibodies are well known in the art. Examples include the flu HA tag polypeptide and its antibody 12CA5 [Field et al., *Mol. Cell. Biol.*, 8:2159–2165 (1988)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Engineeing*, 3(6):547–553 (1990)]. Other tag polypeptides include the Flag-peptide

[Hopp et al., *BioTechnology*, 6:1204–1210 (1988)]; the KT3 epitope peptide [Martin et al., *Science*, 255:192–194 (1992)]; an α-tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA*, 87:6393–6397 (1990)]. Once the tag polypeptide has been selected, an antibody thereto can be generated using the techniques disclosed herein.

Generally, epitope-tagged antagonist may be constructed and produced according to the methods described above. HGF receptor antagonist-tag polypeptide fusions are preferably constructed by fusing the cDNA sequence encoding the HGF receptor antagonist portion in-frame to the tag polypeptide DNA sequence and expressing the resultant DNA fusion construct in appropriate host cells. Ordinarily, when preparing the HGF receptor antagonist-tag polypeptide chimeras of the present invention, nucleic acid encoding the antagonist will be fused at its 3' end to nucleic acid encoding the N-terminus of the tag polypeptide, however 5' fusions are also possible. For example, a polyhistidine sequence of about 5 to about 10 histidine residues may be fused at the N- terminus or the C- terminus and used as a purification handle in affinity chromatography.

Epitope-tagged HGF receptor antagonist can be purified by affinity chromatography using the anti-tag antibody. The matrix to which the affinity antibody is attached may include, for instance, agarose. controlled pore glass or poly(styrenedivinyl)benzene. The epitope-tagged HGF receptor antagonist can then be eluted from the affinity column using techniques known in the art.

In another embodiment ofthe invention, the HGF receptorantagonist may be fused to a salvage receptor binding epitope in order to increase its serum half-life. This may be achieved, for example, by incorporation of a salvage receptor binding epitope into a HGF receptor antagonist antibody fragment (e.g., by mutation of the appropriate region in the antibody fragment or by incorporating the epitope into a peptide tag that is then fused to the antibody fragment at either the end or in the middle, e.g., by DNA or peptide synthesis).

A systematic method for preparing such a chimera having an increased in vivo half-life comprises several steps. The ftrst involves identifying the sequence and conformation of a salvage receptor binding epitope of an Fc region of an IgG molecule. Once this epitope is identified, the sequence of the HGF receptor antagonist of interest is modified to include the sequence and conformation of the identified binding epitope. After the sequence is mutated, the chimera is tested to see if it has a longer in vivo half-life than that of the original antagonist. If the chimera does not have a longer half-life upon testing, its sequence is further altered to include the sequence and conformation of the identified binding epitope.

The salvage receptor binding epitope being incorporated into the HGF receptor antagonist of interest is any suitable such epitope as defmed above, and its nature will depend for example, on the type of antagonist being modified. The transfer is made such that the HGF receptor antagonist of interest still possesses antagonistic activity.

The salvage receptor binding epitope generally constitutes a region wherein any one or more amino acid residues from one or two loops of a Fc domain and is preferably transferred to an analogous position in an HGF receptor antagonist antibody fragment. Preferably, three or more residues from one or two loops of the Fc domain are transferred, and more preferably, the epitope is taken from the CH2 domain of the Fc region of an IgG and transferred to the CH1, CH3, or $V_H$ region, or more than one such region, of the antagonist antibody. Alternatively, the epitope is taken from the CH2 domain of the Fc region and transferred to the $C_L$ region or the $V_L$ region, or both, of the antagonist antibody fragment.

In another embodiment, the chimeric molecule comprises a HGF receptor antagonist fused to an immunoglobulin constant domain or another heterologous polypeptide such as albumin. This includes chimeras in monomeric, homo- or heteromultimeric form. and particularly heterodimeric form.

In general, the chimeric molecules can be constructed in a fashion similar to chimeric antibodies in which a variable domain from an antibody of one species is substituted for the variable domain of another species. See, for example, EP 0 125 023; EP 173,494; Munro, *Nature*, 312:597 (13 Dec. 1984); Neuberger et al., *Nature*, 312:604–608 (13 Dec. 1984); Sharon et al., *Nature*, 309:364–367 (24 May 1984); Morrison et al., *Proc. Nat'l. Acad. Sci. USA*, 81:6851–6855 (1984); Morrison et al., *Science*, 229:1202–1207 (1985); Boulianne et al., *Nature*, 312:643–646 (13 Dec. 1984); Capon et al., *Nature*, 337:525–531 (1989); Traunecker et al., *Nature*, 339:68–70 (1989). Preferably, the Ig is a human immunoglobulin when the chimera is intended for in vivo therapy for humans. DNA encoding immunoglobulin light or heavy chain constant regions is known or readily available from cDNA libraries or can be synthesized. See for example, Adams et al., *Biochemistry*, 19:2711–2719 (1980); Gough et al., *Biochemistry*, 19:2702–2710 (1980); Dolby et al., *Proc. Natl. Acad. Sci.. USA*, 77:6027–6031 (1980); Rice et al., *Proc. Natl. Acad. Sci.*, 79:7862–7865 (1982); Falkner et al., *Nature*, 298:286–288 (1982); and Morrison et al., *Ann. Rev. Immunol.*, 2:239–256 (1984).

Further details of how to prepare such fusions are found in publications concerning the preparation of immunoadhesins. lmmunoadhesins in general, and CD4-Ig fusion molecules specifically, are disclosed in WO 89/02922, published 6 Apr. 1989. Molecules comprising the extracellular portion of CD4, the receptor for human immunodeficiency virus (HIV), linked to IgG heavy chain constant region are known in the art and have been found to have a markedly longer half-life and lower clearance than the soluble extracellular portion of CD4 [Capon et al., supra; Byrn et al., *Nature*, 344:667 (1990)].

In another embodiment, the chimera comprises a HGF receptor antagonist fused to albumin. Such chimeras may be constructed by inserting the entire coding region of albumin into a plasmid expression vector. The DNA encoding the antagonist can be inserted at the 5' end of the albumin sequence, along with an insert encoding a linker consisting of four glycine residues [Lu et al., *FEBS Letters*, 356:56–59 (1994)]. The HGF receptor antagonist-albumin chimera can then be expressed in desired mammalian cells or yeast, for instance.

C. Methods of Treatment and Diarmosis

In another embodiment of the invention, methods for treating cancer are provided. In the methods, HGF receptor antagonist is administered to a mammal diagnosed as having cancer. While the term "cancer" as used herein is not limited to any one specific form of the disease, it is believed that the methods will be particularly effective for cancers which are found to be accompanied by increased levels of HGF, or overexpression or activation of HGF receptor in the mammal. In a preferred method of the invention, the cancer is breast cancer. It is of course contemplated that the methods of the invention can be employed in combination with still other therapeutic techniques such as surgery.

The antagonist is preferably administered to the mammal in a pharmaceutically-acceptable carrier. Suitable carriers and their formulations are described in Remington's *Pharmaceutical Sciences*, 16th ed., 1980, Mack Publishing Co., edited by Oslo et al. Typically, an appropriate amount of a pharmaceutically-acceptable salt is used in the fornmulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antagonist, which matrices are in the form of shaped articles, e.g., films, liposomes or microparticles. It will be apparent to those persons skilled in the art that certain carriers may be more preferable depending upon, for instance, the route of administration and concentration of antagonist being administered.

The antagonist can be administered to the mammal by injection (e.g., intravenous, intraperitoneal, subcutaneous, intramuscular), or by other methods such as infusion that ensure its delivery to the bloodstream in an effective form. The antagonist may also be administered by intratumoral, peritumoral, intralesional, or perilesional routes, to exert local as well as systemic therapeutic effects. Local or intravenous injection is preferred.

Effective dosages and schedules for administering the antagonist may be determined empirically, and making such determinations is within the skill in the art. Those skilled in the art will understand that the dosage of antagonist that must be administered will vary depending on, for example, the mammal which will receive the antagonist, the route of administration, the particular type of antagonist used and other drugs being administered to the mammal. Guidance in selecting appropriate doses for antibody antagonists is found in the literature on therapeutic uses of antibodies, e.g., *Handbook of Monoclonal Antibodies*, Ferrone et al., eds., Noges Publications, Park Ridge, N.J., (1985) ch. 22 and pp. 303–357; Smith et al., *Antibodies in Human Diagnosis and Therapy*, Haber et al., eds., Raven Press, New York (1977) pp. 365–389. A typical daily dosage of the antagonist used alone might range from about 1 µg/kg to up to 100 mg/kg of body weight or more per day, depending on the factors mentioned above.

The antagonist may also be administered to the mammal in combination with effective amounts of one or more other therapeutic agents or in conjunction with radiation treatment. Therapeutic agents contemplated include chemotherapeutics as well as immunoadjuvants and cytokines. Chemotherapies contemplated by the invention include chemical substances or drugs which are known in the art and are commercially available, such as Doxorubicin, 5-Fluorouracil, Cytosine arabinoside ("Ara-C"), Cyclophosphamide, Thiotepa, Busulfan, Cytoxin, Taxol, Methotrexate, Cisplatin, Melphalan, Vinblastine and Carboplatin. The antagonist may be administered sequentially or concurrently with the one or more other therapeutic agents. The amounts of antagonist and therapeutic agent depend, for example, on what type of drugs are used, the cancer being treated, and the scheduling and routes of administration but would generally be less than if each were used individually.

Following administration of antagonistto the mammal, the mammal's cancer and physiological condition can be monitored in various ways well known to the skilled practitioner. For instance, tumor mass may be observed physically or by standard x-ray imaging techniques.

The antagonists of the invention also have utility in non-therapeutic applications. For instance, methods for employing the antagonists in vitro in diagnostic assays are provided. For instance, the antagonists may be employed in diagnostic assays to detect overexpression of HGF receptor in specific cells and tissues. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147–158]. The antagonists used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, 32p, 35S, or $^{125}I$, a fluorescent or chemiluminescent compound. such as fluorescein isothiocyanate, rhodamine. or luciferin, or an enzyme, such as alkaline phosphatase, beta-galactosidase or horseradish peroxidase. Any method known in the art for conjugating the antagonist to the detectable moiety may be employed. including those methods described by Hunter et al., *Nature*, 194:495 (1962); David et al., *Biochemistry*, 13:1014–1021 (1974); Pain et al., *J. Immunol. Meth.*, 40:219–230 (1981); and Nygren, *J. Histochem. and Cytochem.*, 30:407 (1982).

Additionally, the HGF receptor antagonist antibodies can be used to immunopurify HGF receptor(s).

D. Articles of Manufacture and Kits

In a further embodiment of the invention, there are provided articles of manufacture and kits containing materials useful for treating cancer or detecting or purifying HGF receptor. The article of manufacture comprises a container with a label. Suitable containers include, for example, bottles, vials, and test tubes. The containers may be formed from a variety of materials such as glass or plastic. The container holds a composition having an active agent which is effective for treating cancer or for detecting or purifying HGF receptor. The active agent in the composition is a HGF receptor antagonist and preferably, comprises Fab fragments of monoclonal antibodies specific for c-Met. The label on the container indicates that the composition is used for treating cancer or detecting or purifying HGF receptor, and may also indicate directions for either in vivo or in vitro use, such as those described above.

The kit of the invention comprises the container described above and a second container comprising a buffer. It may further include other materials desirable from a commercial and user standpoint, including other buffers, diluents, filters, needles, syringes, and package inserts with instructions for use.

The invention will be more fully understood by reference to the following examples. They should not, however, be construed as limiting the scope of the invention. All reference citations herein are incorporated by reference.

EXAMPLES

All restriction enzymes referred to in the examples were purchased from New England Biolabs and used according to manufacturer's instructions. All other commercially available reagents referred to in the examples were used according to manufacturer's instructions unless otherwise indicated. The source of those cells identified in the following examples, and throughout the specification, by ATCC accession numbers is the American Type Culture Collection, Rockville, Md.

EXAMPLE 1

Preparation of anti-c-Met Antibodies

Balb/c mice (obtained from Charles River Laboratories) were immunized by injecting 2.5 µg/50 µl c-Met-IgG fusion protein (diluted in MPL-TDM adjuvant purchased from Ribi Immunochemical Research Inc., Hamilton, Mont.) five times into each hind foot pad. Injections were administered on Day 0 and Days 56,63, 66 and 73. The c-Met-lgG fuision protein (including the extracellular domain of c-Met fused to a human IgG1 heavy chain) was constructed essentially as described by Mark et al., *J. Biol. Chem.*, 267:26166–26171 (1992) and produced in Chinese hamster ovary (CHO) cells. The c-Met-IgG was subsequently purified in a single step using affinity chromatography on immobilized Protein A (Bioprocessing, Inc., Princeton, N.J.), using an elution scheme modified from Chamow et al., *J. Immunol.*, 153:4268–4280 (1994). Culture supernatant was loaded onto a Protein A column equilibrated in 20 mM Tris, pH 7.4,0.15 M NaCl. The column was washed. first with equilibration buffer, then with equilibration buffer containing 0.5 M tetrarnethylammonium chloride, to remove non-specifically bound protein. c-Met-IgG was eluted with 20 mM Tris, pH 7.4, 3.5 M $MgC_2$. This c-Met-lgG eluate was concentrated and exchanged into 20 mM Tris, pH 7.4, 0.15 M NaCl by gel filtration on Sephadex G25 to a final concentration of about 2–4 mg/ml.

On Day 77, popliteal lymph nodes were removed from the mice and a single cell suspension was prepared in DMEM media (obtained from Biowhitakker Corp.) supplemented with 1% penicillin-streptomycin. The lymph node cells were then fused with murine myeloma cells P3X63AgU.1 (ATCC CRL 1597) using 35% polyethylene glycol and cultured in 96-well culture plates. Hybridomas resulting from the fusion were selected in HAT medium. Ten days after the fusion, hybridoma culture supernatants were screened in an ELISA to test for the presence of monoclonal antibodies binding to the c-Met-IgG fusion protein.

In the ELISA, 96-well microtiter plates (Nunc) were coated by adding 50 μl of 2 μg/ml goat anti-human IgG Fc (purchased from Cappel Laboratories) to each well and incubating at 4° C. overnight. The plates were then washed three times with distilled water. The wells in the microtiter plates were blocked with 200 μl of 2% bovine serum albumin and incubated at room temperature for 1 hour. The plates were then washed again three times with distilled water.

After the washing step, 100 μl of 0.4 μg/ml c-Met-lgG fusion protein (as described above) was added to each well. The plates were incubated for 1 hour at room temperature on a shaker apparatus, followed by washing three times with distilled water.

Then, 100 μl of the hybridoma supernatants was added to designated wells. 100 μl of P3X63AgU.1 myeloma cell conditioned medium was added to other designated wells as controls. The plates were incubated at room temperature for 1 hour on a shaker apparatus and then washed three times with distilled water.

Next, 50 μl HRP-conjugated goat anti-mouse IgG Fc (purchased from Cappel Laboratories), diluted 1:1000 in assay buffer (0.5% bovine serum albumin, 0.05% Tween-20, 0.01 % Thimersol in PBS), was added to each well and the plates incubated for 1 hour at room temperature on a shaker apparatus. The plates were washed three times with distilled water, followed by addition of 50 μl of substrate (5 mg OPD, 12.5 ml PBS, 5 μl $H_2O_2$) to each well and incubation at room temperature for 10 minutes. The reaction was stopped by adding 50 μl of 2 N $H_2SO_4$ to each well, and absorbance at 490 nm was read in an automated microtiter plate reader.

Of 912 hybridoma supernatants screened in the ELISA, 24 supernatants tested positive (calculated as approximately 2 times above background). The supernatants testing positive in the ELISA were further analyzed by FACS analysis using A549 cells (human epidermoid cell line expressing c-Met; ATCC CCL 185) or BaF3 transfected cells expressing c-Met (see Example 6 below) and fluorescein-conjugated mouse anti-IgG. The FACS analysis showed 19/24 supernatants were positive for anti-c-Met antibodies.

EXAMPLE 2

Preparation of anti-c-Met Antibody 5D5.11.6

Balb/c mice were immunized as described in Example 1 except that the c-Met-lgG fusion protein injections were administered on Day 0 and Days 7, 14, 21, 28, 211, 273 and 279. On Day 282, lymph nodes were removed and a fusion was conducted as described in Example 1. Hybridoma supernatants were tested according to the ELISA described in Example 1. One of the positive anti-c-Met monoclonal antibodies was called 5D5.11.6 ("5D5"). Further antibody analysis showed that the 5D5 monoclonal antibody is an IgG1 isotype antibody comprising a kappa light chain.

Ascites was produced in Balb/c mice and the monoclonal antibodies were then purified using a protein G affinity column. The protein concentration was determined by the absorbance at 280 nm using an extinction coefficient of 1.4.

EXAMPLE 3

Inhibition Assay of anti-c-Met Antibody 1A3.3.13 to Block HGF Binding

An inhibition assay was conducted to examine the ability of the antibodies (described in Example 1) to block binding of HGF to c-Met-IgG fusion protein. Prior to conducting the inhibition assay, the 24 hybridoma supernatants determined positive in the ELISA in Example 1 were purified on Protein A-Sepharose columns to yield antibody preparations of about 1 μg/ml.

For the assay, 96-well microtiter plates were coated by adding 100 μl of 2 μg/ml goat anti-human Fc (purchased from Jackson Immunochemical, West Grove, Pa.) in 0.05 M sodium bicarbonate, pH 9.6, to each well and incubating overnight at 4° C. The plates were then washed with a washing buffer (0.05% Tween-20, 0.01% Thimersol in PBS). Nonspecific binding in the wells was blocked by adding 150 μl blocking buffer (0.5% BSA, 0.01% Thimersol in PBS, pH 7.4) to each well and incubating at room temperature for 2 hours with rapid agitation on an orbital shaker.

Next, continuing at room temperature and agitation on the orbital shaker, the blocking buffer was removed from the wells, and the plates were washed with washing buffer. Next, 100 μl of 10 μg/ml c-Met-IgG fusion protein in PBS, 0.5% BSA, 0.05% Tween-20, and 0.01 % Thimersol (described in Example 1) was added to the wells. The plates were incubated for 2 hours and then washed 3 times with washing buffer.

Recombinant human HGF (rhuHGF) was produced in CHO cells using a procedure modified from Naka et al., *J. Biol. Chem., 267:20114–20119* (1992). rhuHGF-transfected cells were grown in a 400 L bioreactor in medium containing 2% fetal bovine serum for 8 days. Culture supernatant containing rhuHGF was concentrated and clarified, then conditioned by the addition of solid NaCI to 0.3 M. rhuHGF was then purified in a single step using cation exchange chromatography. Conditioned, concentrated culture supernatant was loaded onto a column of S-Sepharose Fast Flow equilibrated in 20 mM Tris, pH 7.5,0.3 M NaCl. After washing out unbound protein, rhuHGF was eluted in a linear gradient from 20 mM Tris, pH 7.5, 0.3 M NaCl to 20 mM Tris, pH 7.5, 1.2 M NaCl. rhuHGF-containing fractions were pooled based on SDS-PAGE analysis. The S Sepharose Fast Flow pool was concentrated and exchanged into 20 mM Tris, pH 7.5, 0.5 M NaCl by gel filtration on Sephadex G25 to a final concentration of about 3–5 mg/mi. A rhuHGF stock solution was then prepared by diluting the rhuHGF in assay buffer (0.5% bovine serum albumin, 0.05% Tween-20. 0.01% Thimersol in PBS) to a concentration of 10 µg/ml. A stock solution of control gp120 antibody (Genentech. Inc.) was also prepared by diluting the antibody in assay buffer to a concentration of 10 µg/ml.

Then, 50 µl of either rhuHGF, gp120 antibody or one of the 24 monoclonal antibodies was added to designated wells to yield a final concentration of 1000, 100, 10, or 1 ng/ml/well. Immediately, 50 µl of 200 ng/ml biotinylated rhuHGF (rhuHGF biotinylated using Biotin-X-NHS obtained from Research Organics. Inc., Cleveland, Ohio) was also added to each well. After 2 hours incubation, the wells were washed 3 times with washing buffer. 100 µl HRP-streptavidin (1:2000 dilution in assay buffer) (purchased from Zymed Laboratories), was added to the wells and the plates were incubated for 30 minutes. The plates were washed again 3 times with washing buffer. 50 µl of substrate (5 mg OPD. 12.5 ml PBS, 5 µl $H_2O_2$) was added to the wells and color was allowed to develop for 20 minutes. The reaction was stopped by adding 100 µl 4.5 N sulfuric acid to each well. Absorbance at 492 nm was quantitated in an automated microtiter plate reader.

One of the monoclonal antibodies, referred to as 1A3.3.13, significantly blocked binding of HGF (FIG. 2). Further antibody analysis showed that the 1A3.3.13 monoclonal antibody is an IgG1 isotype antibody comprising a kappa light chain.

EXAMPLE 4

Mitogenic Assay of Antibodies 3 D6, 6G1 and 1A3.3.13 on Human Mammary Epithelial Cell Line

Several different antibodies produced in the fusion described in Example 1, referred to as 3D6, 6G1, and 1A3.3.13, and purified as described in Example 3, were tested and compared for their ability to induce DNA synthesis in a human mammary epithelial cell bioassay.

Human mammary epithelial cells (obtained from Clonetics Corp., No. CC-255 1) were passaged in Mammary Epithelial Cell Basal Medium (Clonetics Corp., No. CC-3151). Prior to conducting the bioassay, the cells were trypsinized, washed, and resuspended in assay medium (Basal Medium supplemented with 1 mg/ml BSA, penicillin, streptomycin and L-glutamine) to a concentration of $1\times10^5$ cells/ml. Next, 100 µl of the cells were added to the wells of 96-well culture plates. rhuHGF (described in Example 3) was diluted in assay medium at concentrations of 20 ng/ml and 200 ng/ml. The 3D6, 6G 1, 1A3.3.13, and control gp 120 antibodies were diluted in assay medium at concentrations of 200 ng/ml and 2 µg/ml. 100 µl of the rhuHGF and antibody preparations was then added to designated wells. The plates were incubated at 37° C. in 5% $CO_2$ for 16 hours.

Next, 1 µCi $^3$H-thymidine (Amersham) was added to each well. and the plates were incubated for 24 hours at 37° and 5% $CO_2$. The human mammary epithelial cells were harvested and the amount of radioactivity incorporated into the DNA was then quantitated in a microplate scintillation counter.

Figure 3:
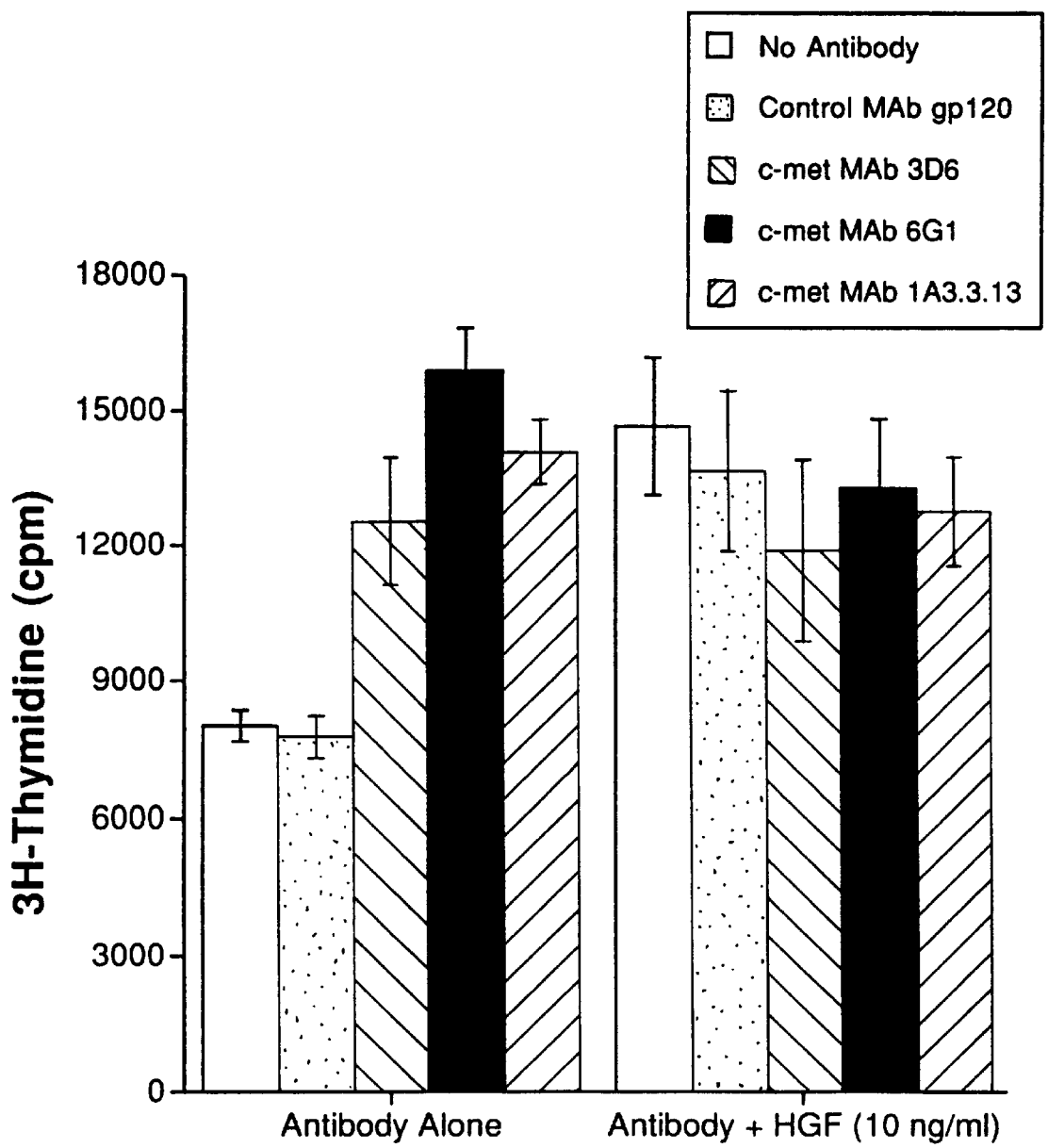
FIG. 3 is a bar diagram showing the stimulatory effect of monoclonal antibodies 3D6. 6G 1, and 1A3.3.13 on human mammary epithelial cells in a proliferation assay.

The results showed that, at a concentration of 10 ng/ml, the 3D6,6G1 and 1A3.3.12 antibodies have some HGF agonistic effect. (See FIG. 3)

EXAMPLE 5

Mitogenic Assay of Antibodies 05–237 and 05–238 on Mink Lung Cell Line

Anti-c-Met antibodies 05–237 and 05–238 (purchased from Upstate Biotechnology Inc., Lake Placid, N.Y.; see also, Prat et al., *Mol. Cell. Biol.*, supra, Prat et al., *Int. J. Cancer*, supra) and antibody 3D6 (described in Example 4) were tested and compared for their ability to induce DNA synthesis in a mink lung bioassay.

Mink lung cells (Mv 1 Lu, ATCC CCI 64) were passaged in DME/F12 (50:50) supplemented with 10% fetal bovine serum, penicillin, streptomycin and L-glutamine. Prior to conducting the bioassay, the mink lung cells were trypsinized. washed, and resuspended in assay medium (DME/F12 medium supplemented with 1 mg/ml BSA, penicillin, streptomycin and L-glutamine) to a concentration of $1\times10^5$ cells/ml. The bioassay was then conducted as described in Example 4.

Figure 4:
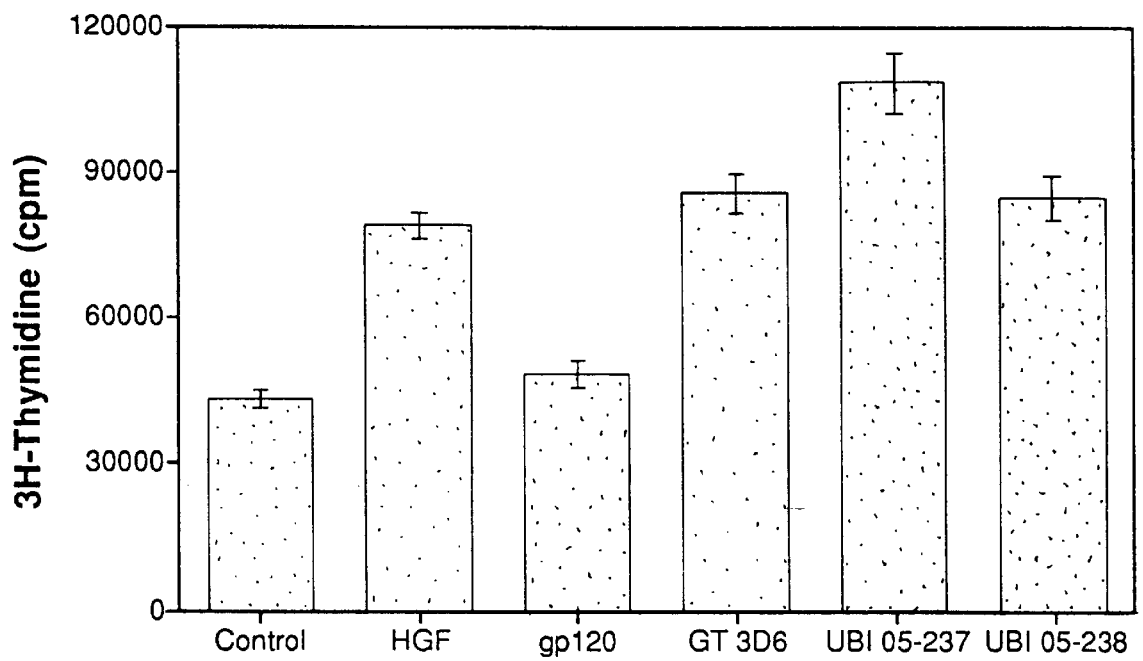
FIG. 4 is a bar diagram showing the stimulatory effect of monoclonal antibodies 3D6, 05–237 and 05–238 on mink lung cells in a proliferation assay.

The results showed that antibodies 05–237 and 05–238 have HGF agonistic effect. (See FIG. 4)

EXAMPLE 6

Antagonistic Activity of Monoclonal Antibody 1A3.3.13 Fab

Antagonistic activity of 1A3.3.13 monoclonal antibody Fab fragments was determined using a thymidine incorporation assay. Monoclonal antibody 1A3.3.13 (described in Example 3) was digested with papain to obtain the Fab fragments. The papain digestion was performed by initially dialyzing the antibody against a 20 mM phosphate/b mM EDTA, pH 7.0, buffer overnight. The antibody was then concentrated to approximately 10 mg/ml. Next, 0.5 ml immobilized papain (crosslinked 6% beaded agarose, obtained from Pierce Chemicals) was added to a 16×100 mm tube. The papain beads were washed 2 times with 4 ml of digestion buffer (42 mg cysteine-HCl in 12 ml phosphate buffer, pH 10). Each wash was removed using a separator. About 0.5 to 1 ml of the 1A3.3.13 antibody was added to the papain beads and then incubated in a heated shaker bath (37° C., 200 rpm) overnight. 1.5 ml of binding buffer (Immunopure IgG Binding Buffer obtained from Pierce Chemicals) was added to the tube, and the supernatant was separated from the beads with a separator. The supernatant was then passed over a Protein A column equilibrated with the binding buffer. Additional binding buffer was passed over the column and the eluate containing the Fab fragments was collected in 1 ml fractions. The fractions were analyzed by absorbance at 280 nm and the Fab containing fractions dialyzed against PBS overnight. Absorbance at 280 nm was read again to determine the concentration of Fab (about 1.53). The fractions were also run on a 7.5% SDS gel to determine the purity of the Fab in the fraction. The 1A3.3.13 Fab fragments were further tested in an inhibition assay (as described in Example 3). The Fab fragments did inhibit HGF binding but showed a weaker inhibitory effect as compared to intact 1A3.3.13 antibody (data not shown).

An expression plasmid was prepared by inserting a full-length cDNA for human c-Met (described as pOK met cDNA in Rodrigues et al., sunra) into a pRK5.tk.neo vector [de Sauvage et al., *Nature* 369:533–538 (1994); Gorman, *DNA Cloning: A New Approach,* 2:143–90 (IRL Washington 1985)]. The resulting plasmid was linearized and transfected into the IL-3 dependent cell line, BaF3 [Palacios et al., *Cell,* 41:727–734 (1985)] by electroporation (800 microfarad, 250 V, BRL electroporator). Selection of transfectants was performed by culturing the cells for 2–3 weeks in the presence of 2 mg/ml G418. One of the selected transfectant cell lines, referred to as BaF3-hmet.8, was confirmed by Western blotting to express c-Met. BaF3-hmet.8 also tested positive for response to HGF in a proliferation assay measuring incorporation of $^3$H-thymidine. Neither the parental BaF3 cells nor any cells derived by transfection with the pRK5.tk.neo vector alone ("BaF3-neo") were found to express c-Met or respond to HGF in the proliferation assay.

The BaF3-hmet.8 cells were passaged in RPMI medium supplemented with 10% fetal bovine serum, 5% WEHI-conditioned medium (as a source of IL-3) and 2 mM glutamine. Prior to conducting the assay, the cells were washed twice with assay medium (RPMI medium supplemented with 10% fetal bovine serum) and resuspended in assay medium to a concentration of $5\times10^4$ cells/ml. Next, 100 µl of the cells was added to each well in the 96-well culture plates. Various concentrations (0.2 µg/ml, 2 µg/ml, 20 µg/ml) of control gp 120 Fab fragments (gp 120 monoclonal antibody digested with papain as described above) and the 1A3.3.13 Fab fragments were prepared in assay medium and 100 µl was added to designated wells. The plates were incubated at 37° C. in 5% $CO_2$ for 15 hours.

One µCi $^3$H-thymidine was added to each well of the culture plates. The cells were harvested 7 hours later and the amount of radioactivity incorporated into the DNA was quantitated (CPM) in a microplate scintillation counter.

Figure 5:
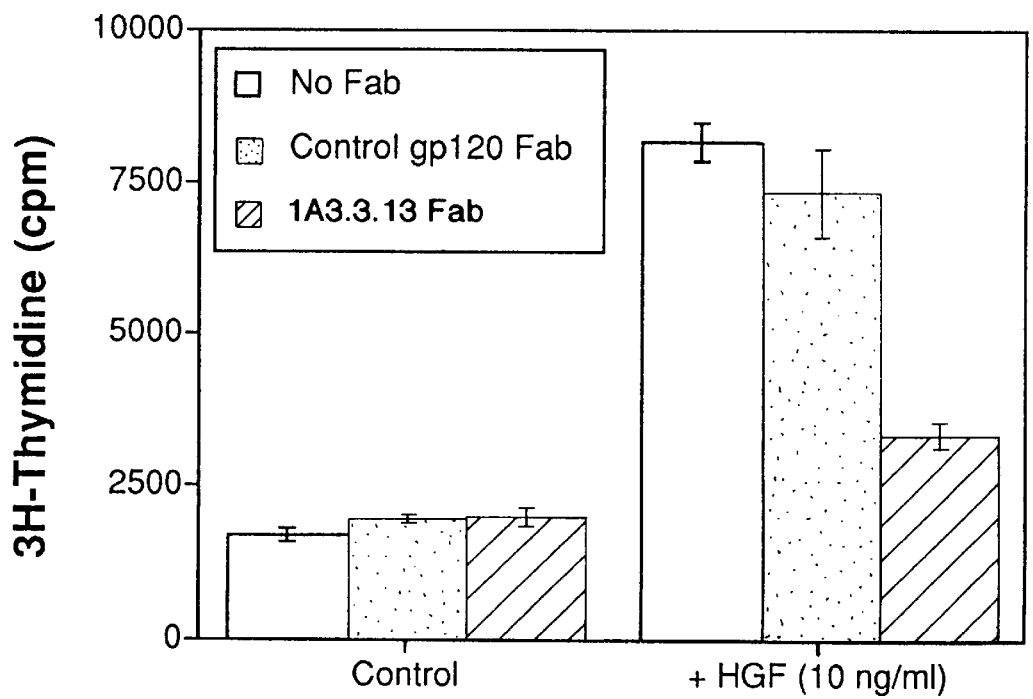
FIG. 5 is a bar diagram showing the inhibitory effect of monoclonal antibody 1A3.3.13 Fab fragments on BaF3-hmet.8 cells in a proliferation assay.

The results are shown in FIG. 5. At a concentration of 10 µg/ml, the 1A3.3.13 Fab fragments significantly blocked BaF3-hmet.8 cell proliferation in the presence of HGF.

EXAMPLE 7

Preparation of 5D5 Antibody Fab

The 5D5 monoclonal antibody (as described in Example 2) was dialyzed and digested with papain essentially as described in Example 6 except that after dialysis. the antibody was concentrated to 7 mg/ml using a Centricon 30 filter. After dialyzing the 5D5 Fab fragments against PBS overnight, the preparation of 5D5 Fab fragments was further purified by gel filtration (Superose™ 12, Pharmacia) to remove residual F(ab')$_2$.

EXAMPLE 8

Assay of 5D5 Antibody and 5D5 Fab Bindint to c-Met

Figure 6A:
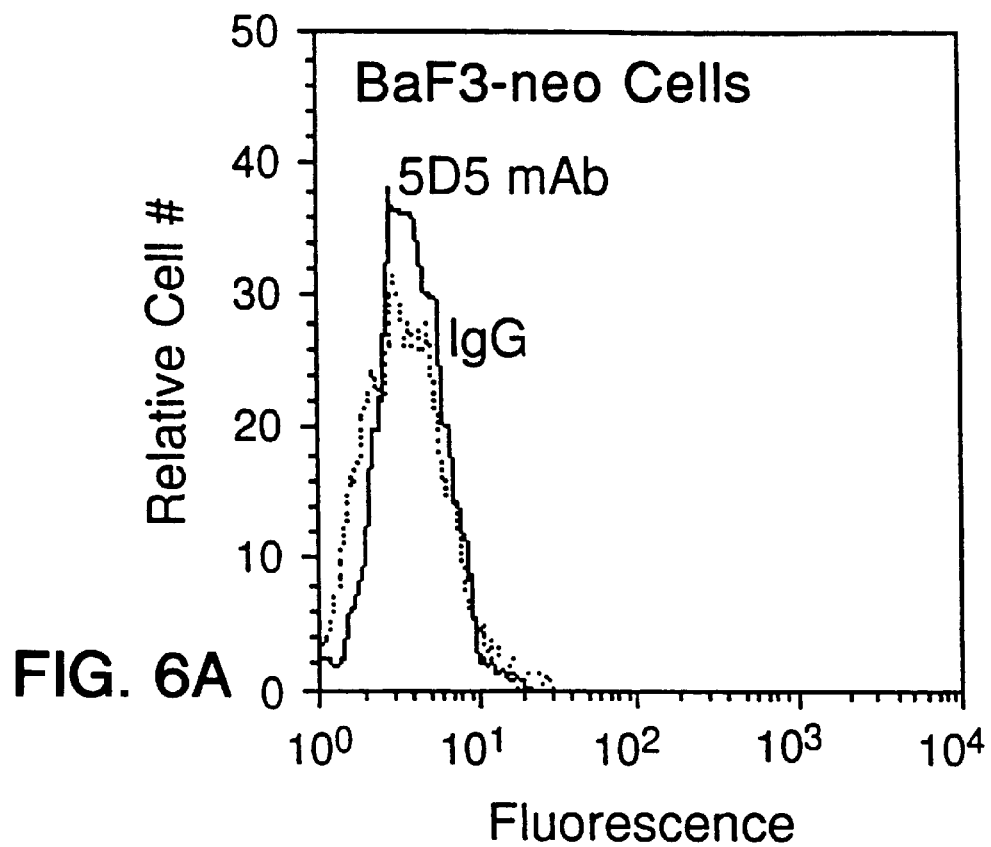
FIGS. 6A and 6B are FACS analysis graphs showing binding specificity of monoclonal antibody 5D5 to BaF3-hmet.8 cells expressing c-Met.
Figure 6B:
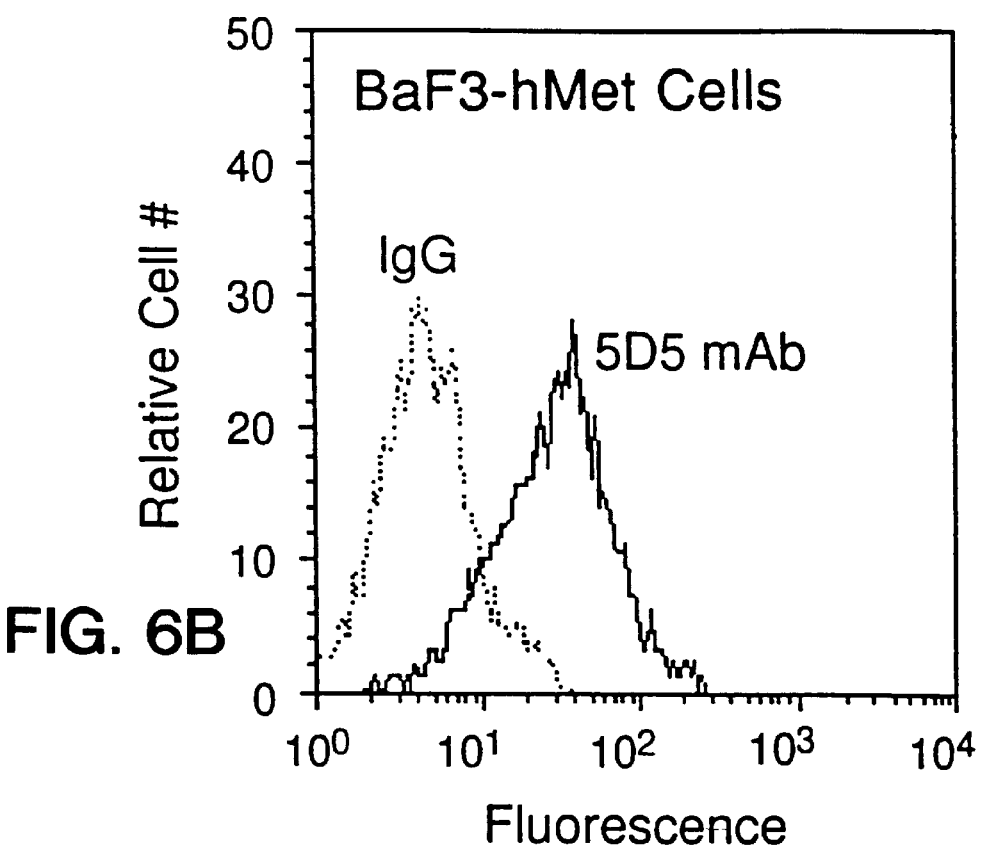

The binding specificity of the 5D5 antibody (described in Example 2) was examined by incubating BaF3-hmet cells or BaF3-neo cells (each described in Example 6) with saturating concentrations of 5D5 antibody or a control IgG, followed by fluorescein-conjugated mouse anti-IgG. 10 4µg/ml 5D5 antibody was incubated with 50 µl of $1\times10^5$ BaF3-hmet cells or BaF3-neo cells for 30 minutes at 4° C. in cell sorting buffer (PBS and 1% fetal calf serum). The cells were washed twice with cell sorting buffer and spun at 1500 rpm for 5 minutes. The cells were then incubated with 100 µl goat (Fab')2 anti-mouse IgG Fc (Cappel) at a 1:1000 dilution for 30 minutes at 4° C. The cells were again washed twice with cell sorting buffer and spun at 1500 rpm for 5 minutes. The cells were then transferred to microtiter tubes with 250 µl of cell sorting buffer and analyzed by flow cytometry with a Becton Dickinson FACScan. As shown in FIGS. 6A and 6B, the 5D5 antibody binds to the BaF3-hmet cells but not to the BaF3-neo cells, indicating that 5D5 antibody binds c-Met.

Figure 7:
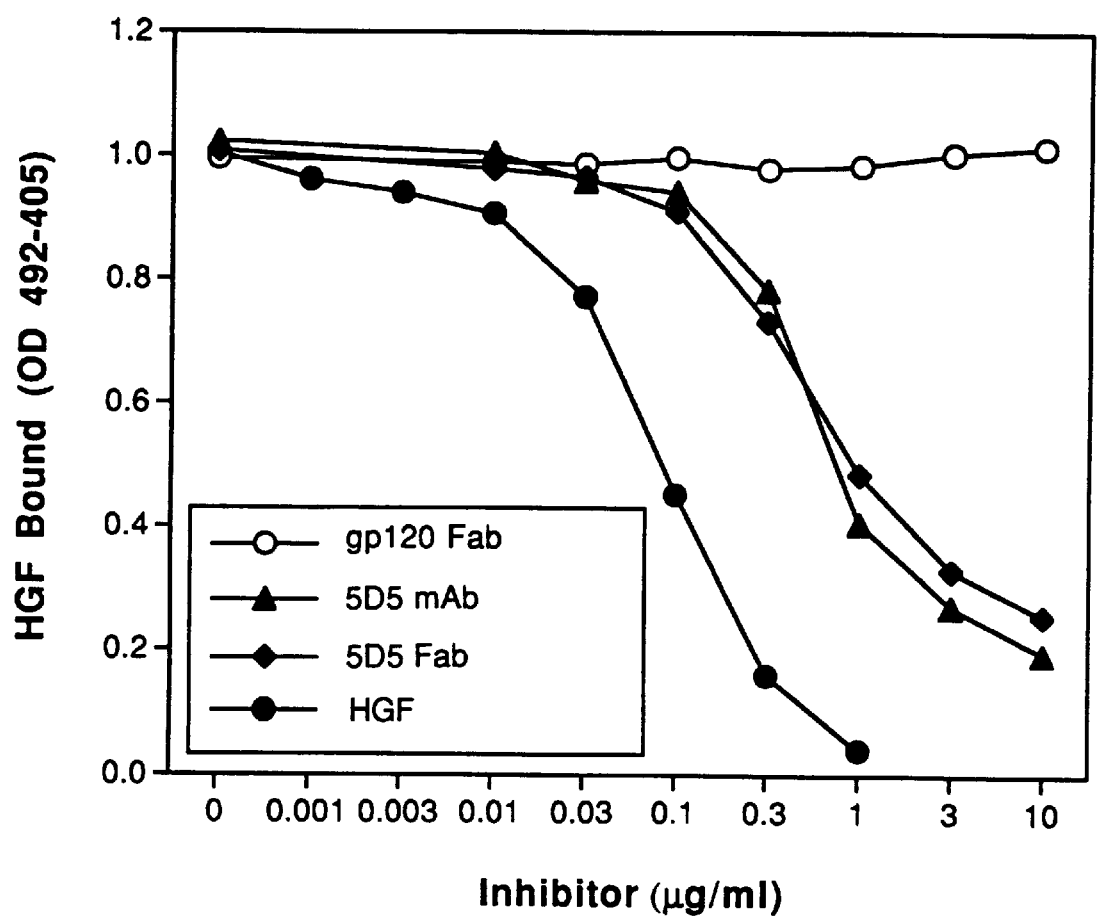
FIG. 7 is a graph showing the inhibition of HGF binding to c-Met-IgG fusion protein by monoclonal antibody 5D5 and by 5D5 Fab.

An inhibition assay was also conducted, essentially as described in Example 3, to examine the ability of 5D5 antibody (Exanple 2) and 5D5 Fab (described in Example 7) to block binding of HGF to c-Met-IgG fusion protein. rhuHGF, 5D5 antibody, 5D5 Fab and control gp 120 Fab were tested at concentrations ranging from 0 to 10 µg/ml, as shown in FIG. 7. Each data point in the graph of FIG. 7 is the mean of triplicates. The data illustrated in FIG. 7 shows that both the 5D5 antibody and 5D5 Fab blocked binding of HGF to c-Met-IgG.

EXAMPLE 9

Antagonistic Activity of 5D5 Fab
A. BaF3-hmet Cell Assay

Figure 8B:
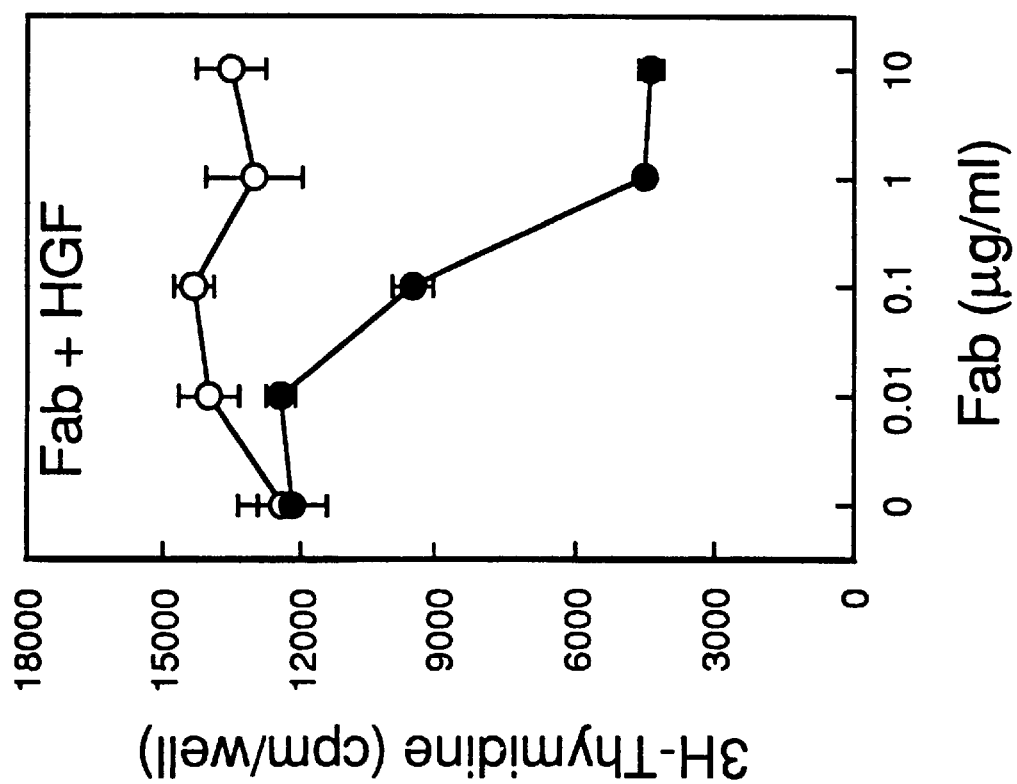
FIGS. 8A and 8B are graphs showing the inhibitory effect of 5D5 Fab on BaF3-hmet.8 cells in a proliferation assay.
Figure 8A:
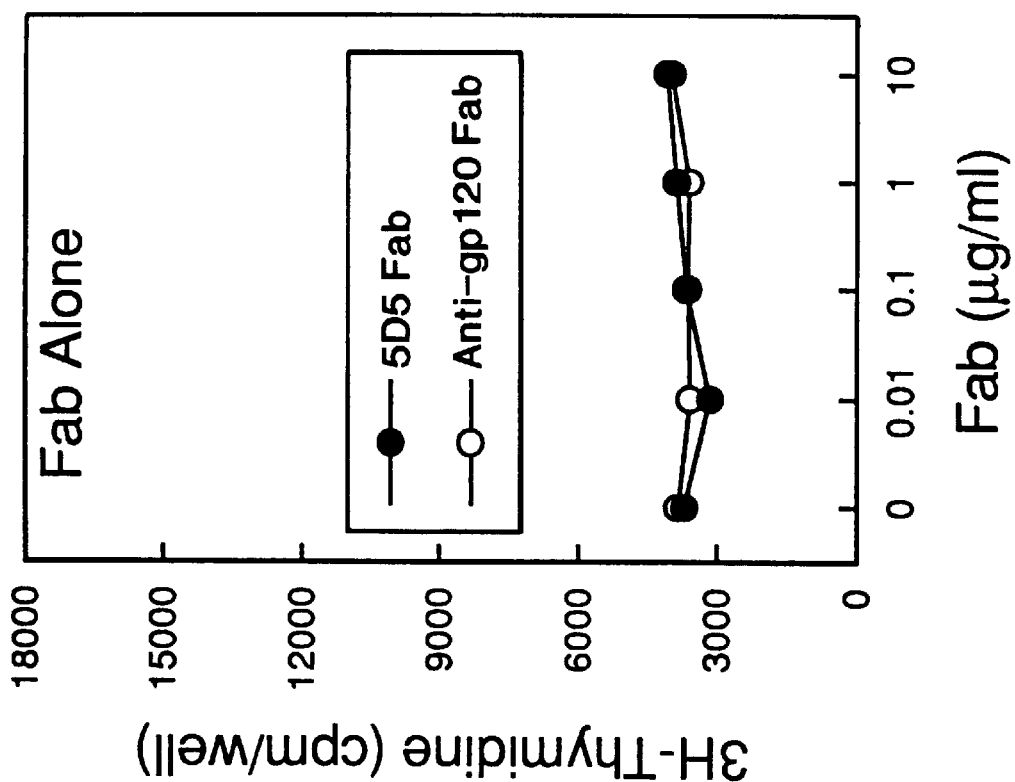
Figure 9:
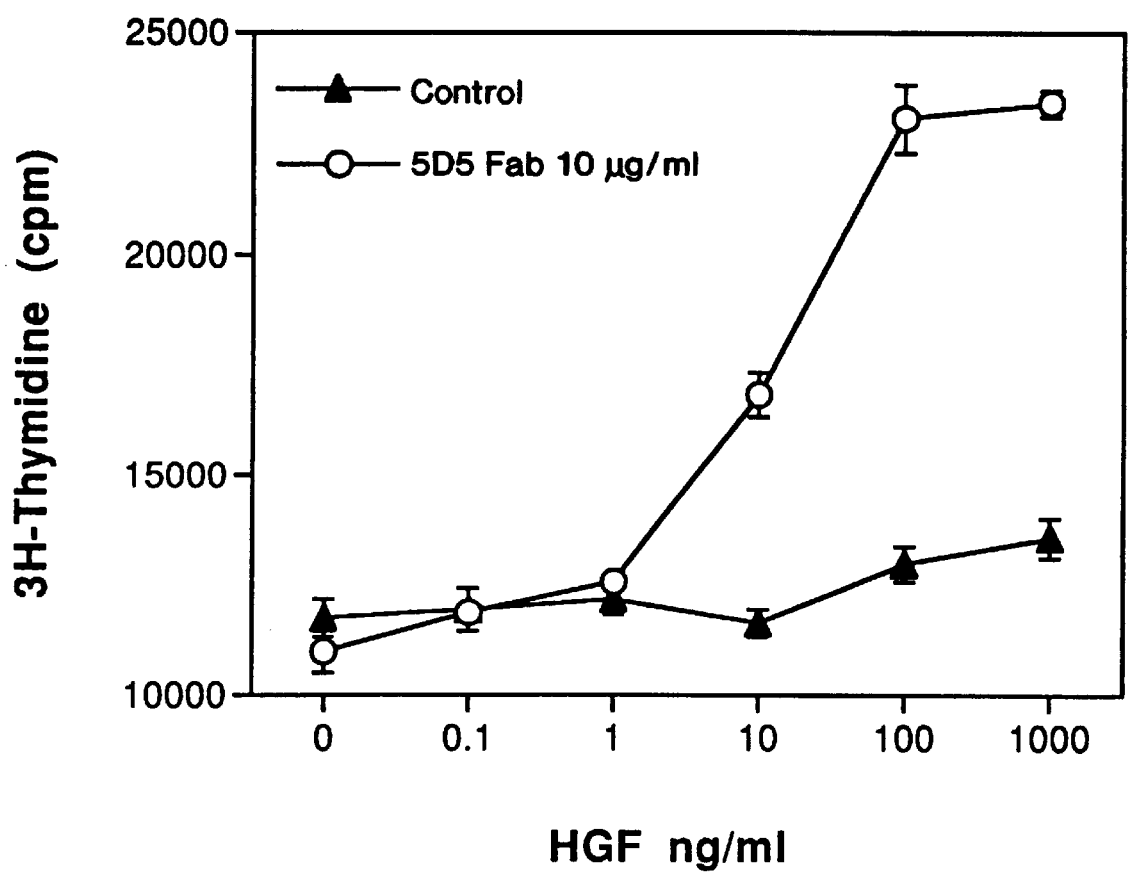
FIG. 9 is a graph showing the inhibitory effect of 5D5 Fab on a human breast carcinoma cell line (MDA-MB435) which expresses c-Met.

Antagonistic activity of 5D5 Fab fragments was examined using a thymidine incorporation assay, as described in Example 6. Various concentrations (0, 0.01,0.1, 1, 10 µg/ml) of control gp 120 Fab and 40 5D5 Fab (Example 7) were prepared in the assay medium and added to designated wells, either alone or in the presence of 10 ng/ml rhuHGF. The results are shown in FIGS. 8A and 8B. Data are the mean ±SEM of4 replicates in a representative experiment. As shown in FIGS. 8A and 8B, the 5D5 Fab acts as an antagonist at concentrations as low as 1 µg/ml, significantly blocking BaF3-hmet cell proliferation in the presence of HGF.
B. Human Mammary Tumor Cell Assay Antagonistic activity of 5D5 Fab fragments was examined in a mitogenic assay to measure induction of DNA synthesis in a human breast carcinoma cell line. MDA-MB435 human breast carcinoma cells (ATCC HTB 129) (which express c-Met) were cultured in DMEM, 5% fetal bovine serum, 100 U/ml penicillin, 100 µg/ml streptomycin sulfate and 2 mM glutamine. Prior to conducting the assay, the cells were washed and resuspended in assay medium (DMEM, 0.1% BSA, 2 mM glutamine). The cells were then plated in a 96 well plate at 5,000 cells/well and incubated at 37° C. with varying concentrations of rhuHGF (0, 0.1, 1, 10, 100. 1000 ng/ml) in the absence or presence of 10 µg/ml 5D5 Fab (Example 7) overnight. Next, 1 µCi $^3$H-thymidine was added to each well and the plates were incubated for 24 hours at 37° C. The cells were then harvested and the amount of radioactivity incorporated into the DNA was quantitated in a microplate scintillation counter. The results are shown in FIG. 9. Data are the mean ±SEM of 6 replicates in a representative experiment. As shown in FIG. 9, the mitogenic response of the carcinoma cells to the HGF was completely blocked by 5D5 Fab.

EXAMPLE 10

Effect of 5D5 Fab on Tyrosine Phosphorylation of c-Met

The ability of 5D5 Fab to stimulate the c-Met receptor or induce c-Met activation was examined in an in vitro assay measuring c-Met tyrosine phosphorylation. Phosphorylation of c-Met was measured in a sandwich ELISA, based on the methods of Sadick et al. in which solubilized c-Met is captured onto a plate coated with rabbit anti-c-Met polyclonal IgG and detected with anti-P-Tyr [Sadick et al., *Anal. Biochem.*, 235:207–214 (1996)]. Microtiter plates were coated overnight at 4° C. with 5 µg/ml rabbit anti-c-Met polyclonal IgG, then non-specific binding was blocked as described in Example 3. While the microtiter plates were coated, A549 cells (described in Example 1) were plated into 100 mm dishes. The next day the cells were washed twice with assay medium (MEM supplemented with 1% BSA) and then challenged for 10 minutes with NK1 (1 µg/ml) [NK1 prepared as described in Lokker et al., *J. Biol. Chem.*, 268:17145–17150 (1993)] or 5D5 Fab alone (10 µg/ml) (Example 7) or with rhuHGF (10 ng/ml) (Example 3). The cells were washed twice with PBS, and then lysed in 1 ml lysis buffer (PBS, 0.2% Triton X-100, 10 µg/ml aprotonin, 5 mM NaF, 2 mM sodium orthovanadate, and 0.2 mM PMSF) for 30 minutes on an orbital shaker at room temperature. The lysate was centrifuged for 10 minutes and 100 µl supernatant was transferred in duplicate to the blocked microtiter plates. After incubation for 2 hours at 23° C., tyrosine phosphorylation was detected by incubation for 2 hours at 23° C. with biotin-anti-P-Tyr (Upstate Biotech, Lake Placid, N.Y.), followed by HRP-streptavidin. Next, TMB peroxidase substrate (KPL, Gaithersburg, Md.) was added. The reaction was stopped with phosphoric acid and OD was measured at 450 nm in an automatic plate reader. Total c-Met was measured in parallel wells incubated as above except that detection was with biotinylated rabbit anti-c-Met polyclonal IgG (NIHS biotin, Pierce Chemical).

Figure 10A:
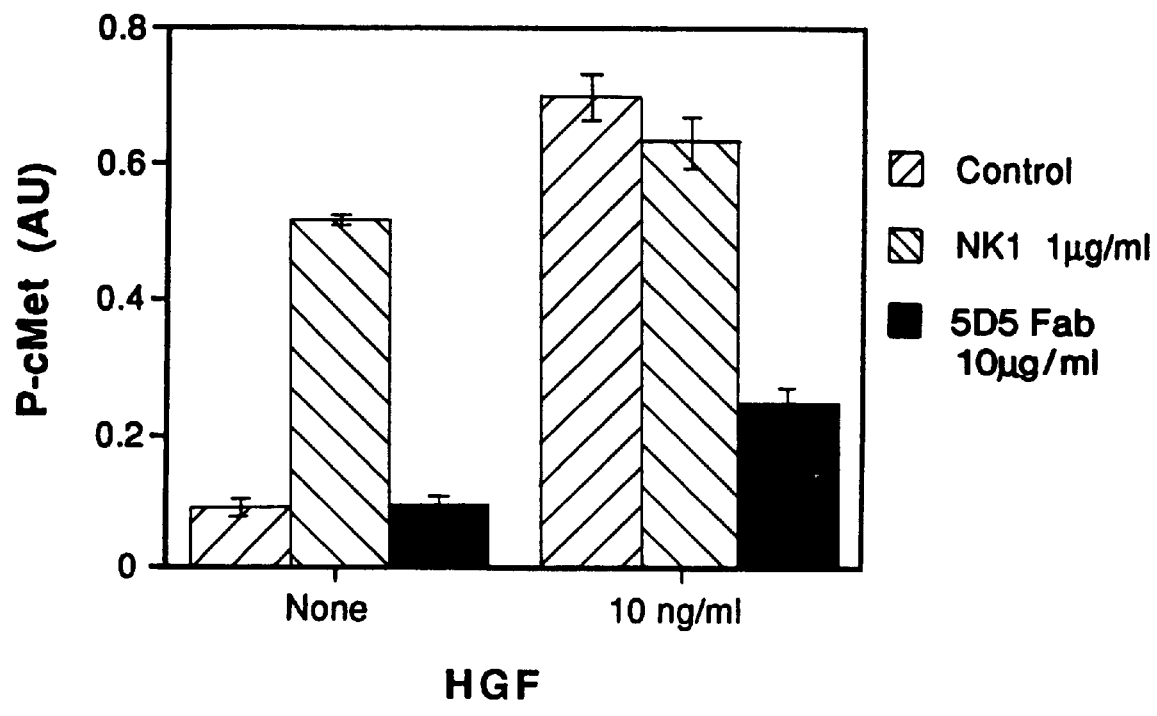
FIGS. 10A and 10B are bar diagrams showing the inhibitory effect of 5D5 Fab on c-Met tyrosine phosphorylation.
Figure 10B:
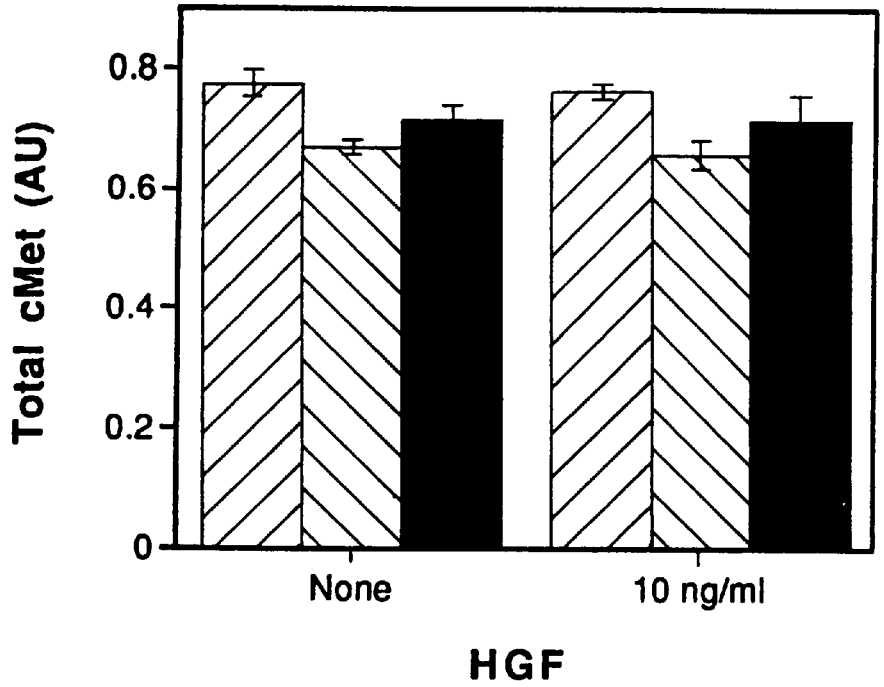

As shown in FIGS. 10A and 10B, lysates were analyzed for relative amounts of tyrosine phosphorylated c-Met (FIG. 10A) and total c-Met (FIG. 10B). Results shown in FIGS. 10A and 10B are the mean ±SEM of 4 replicates from a representative experiment.

NK1 did stimulate tyrosine phosphorylation of c-Met (indicating agonistic activity), but did not significantly inhibit the response of A549 cells to the HGF. In contrast, 5D5 Fab had no stimulatory effect on tyrosine phosphorylation and blocked HGF responses.

EXAMPLE 11

Effect of Heparin on Antagonistic Activity of 5D5 Fab

Figure 11C:
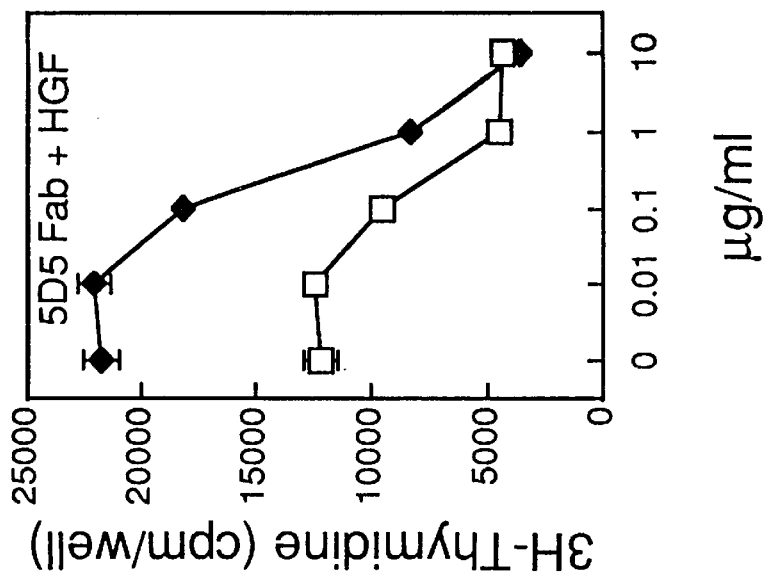
FIGS. 11A–11C are graphs comparing inhibitory effects of NK1 (FIG. 11A), 5D5 Fab (FIG. 11B), and 5D5 Fab and rhuHGF (FIG. 11C) on BaF3-hmet.8 cells in a proliferation assay conducted in the presence or absence of heparin.
Figure 11B:
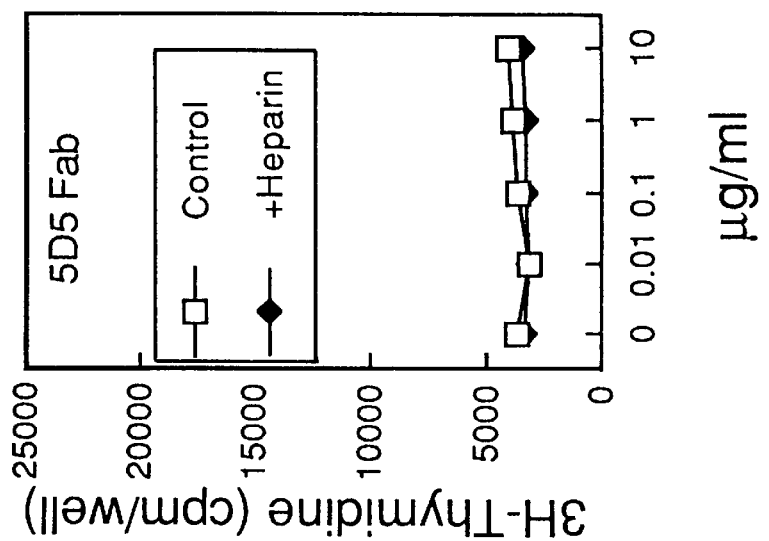

The effect of heparin on the antagonistic activity of 5D5 Fab was examined using a thymidine incorporation assay, as described in Examples 6 and 9 except that BaF3-hmet cells were incubated with NK1 (described in Example 10; 0, 0.0 1, 0.1, 1 µg/ml), 5D5 Fab (described in Example 7; 0, 0.0 1, 0.1, 1, 10 µg/ml) or 5D5 Fab and 10 ng/ml HGF. Each incubation was done in the absence or presence of heparin (1 µg/ml) (Sigma). The results, shown in FIGS. 11A–11C, are the mean ±SEM of 4 replicates from a representative experiment.

Figure 11A:
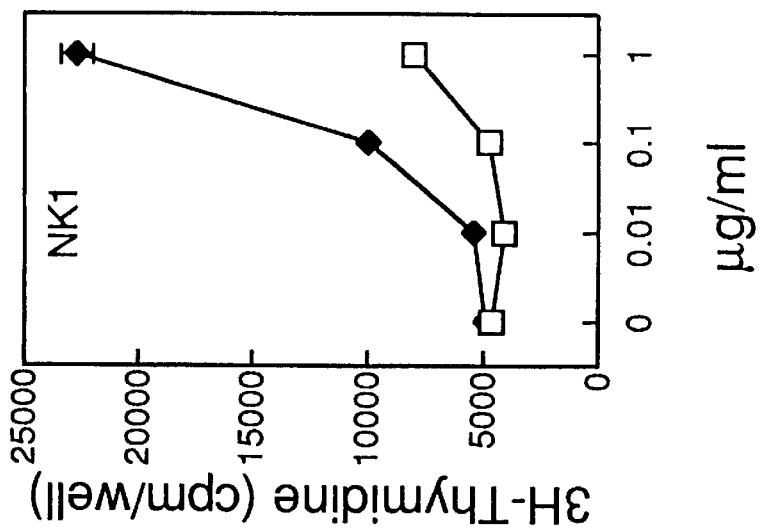

As shown in FIG. 11A, NK1 can be converted to an agonistic molecule by the presence of exogenous heparin. In contrast, heparin did not confer agonist activity on the 5D5 Fab (FIG. 11B). Although the response to HGF was enhanced by heparin, the 5D5 Fab remained an antagonist and completely blocked HGF activity (FIG. 11C).

EXAMPLE 12

Effect of 5D5 Fab on HGF-lnduced Cell Migration

An assay was conducted to examine the ability of 5D5 Fab to inhibit HGF-induced cell migration. A549 cells (described in Example I) were added to the upper wells of a 48-well modified Boyden chamber (NEURO PROBE INC., Cabin John, Md.) containing rhuHGF (10 ng/ml) and/or 5D5 Fab (Example 70;10 µg/ml) in the lower wells. A barrier of polyvinylpyrrolidone-free polycarbonate filter with 8 micron pore size was employed. After incubation for 6 hours at 37° C., the cells on the upper surface of the membrane were scraped off, and the membrane was stained with DifQuik™ (Baxter Scientific Products). A549 cells that had migrated onto the lower side of the membrane were counted in 20 randomly selected fields for each well. The data shown in Table 1 below are the mean ±SD of 4 wells.

TABLE 1

Inhibition of HGF-induced migration by 5D5 Fab
Number of Cells Migrated per High Powered Field

|  | Experiment 1 | Experiment 2 |
| --- | --- | --- |
| Control | 0 ± 0 | 9 ± 8 |
| HGF | 224 ± 30 | 35 ± 10 |
| 5D5 Fab | 2 ± 2 | 7 ± 4 |
| HGF + 5D5 Fab | 37 ± 22 | 6 ± 4 |

The results show that 5D5 Fab blocked migration responses to HGF.

EXAMPLE 13

Sequencing, Cloning and Expression of 5D5 Fab

An aliquot of 5D5 Fab (Example 7) was resolved on a 4–20% gradient SDS gel and electroblotted onto a PVDF (Immobilon-PSQ) membrane (Millipore, Marlborough, Mass.) for 1 hour at 250 mA constant current in a BioRad Trans-Blot transfer cell [Matsudaira, *J. Biol. Chem.*, 262:10035–10038 (1987)]. The membrane was then stained with 0.1% Coomassie Blue R-250 in 50% methanol for 30 seconds and destained for 2–3 minutes with 10% acetic acid in 50% methanol. After destaining, the membrane was thoroughly washed with water and allowed to dry before sequencing on a model 473A automated protein sequencer, using a Blott TM cartridge (Applied Biosystems). Peaks were integrated with Justice Innovation software using Nelson Analytical 760 interfaces and sequence interpretation was performed on a DEC alpha [Henzel et al., *J. Chromatoraphy*, 404:41–52 (1996)].

Obtaining sequence of the 5D5 heavy chain required deblocking, which was performed as follows. The Fab fragment was reduced with 7 mM DTT at 45° C. for 1 hour and alkylated with 180 mM isopropylacetamide at 25° C. for 20 minutes [Krutzsch et al., *Anal. Biochem.*, 209:109–116 (1993)]. The alkylated Fab fragment was then exchanged 3× in a Microcon-I 0 with 0.1 M sodium phosphate containing 10 mM DTT (in digestion buffer) and digested with 1 mU of pyroglumate aminopeptidase (Takara Biochemicals, Berkeley, Calif.) at 45° C. for 3 hours in 20 µl digestion buffer. The deblocked Fab was then transferred to the PVDF membrane and sequenced as described above.

N-terminal sequence data were used to design PCR primers specific for the 5' ends of the variable regions of the light and heavy chains, while 3' primers were designed to anneal to the concensus framework 4 of each chain [Kabat et al., *Sequences of Proteins of Immunological Interest*, Public Health Service, National Institutes of Health, Bethesda, Md., (1991)]. The primers were also designed to add restriction enzyme sites for cloning. Total RNA, extracted from $10^8$ cells of hybridoma 5D5 with a Stratagen RNA isolation kit, was used as substrate for RT-PCR. Reverse transcription was performed under standard conditions [Kawasaki et al., *PCR Protocols:A Guide to Methods and Applications*, Innis et al., eds., Academic Press, San Diego, pp. 21–27 (1990)] using the framework 4 specific primers and Superscript II RNase H-Reverse Transcriptase (Gibco-BRL, Gaithersburg, Md.). PCR amplification employed Taq polymerase (Perkin Elmer-Cetus, Foster City, Calif.), as described in Kawasaki et al., supra, except that 2% DMSO was included in the reaction mixture. Amplified DNA fragments were digested with restriction enzymes SfiI and RsrII (light chain) or MluI and ApaI (heavy chain), gel purified, and cloned into a derivative of expression plasmid pAK19 [Carter et al., *Bio/Technology*, 10:163–167 (1992)]. This vector, pXCA730, was modified by site-directed mutagenesis [Kunkel et al., *Proc. Natl. Acad. Sci.*, 82:488 (1985)] to contain unique restriction sites between the STII signal sequences and the variable domains, and at the junction of the variable and constant domains of each chain. The light and heavy chain variable domain cDNAs were inserted upstream and in frame to human CK and CHI domains. The C-terminal cysteine of the heavy chain in pAK19, which could form a disulfide bridge to give F(ab')$_2$ molecules, was removed to permit expression of only the Fab form of the antibody.

Figure 12:
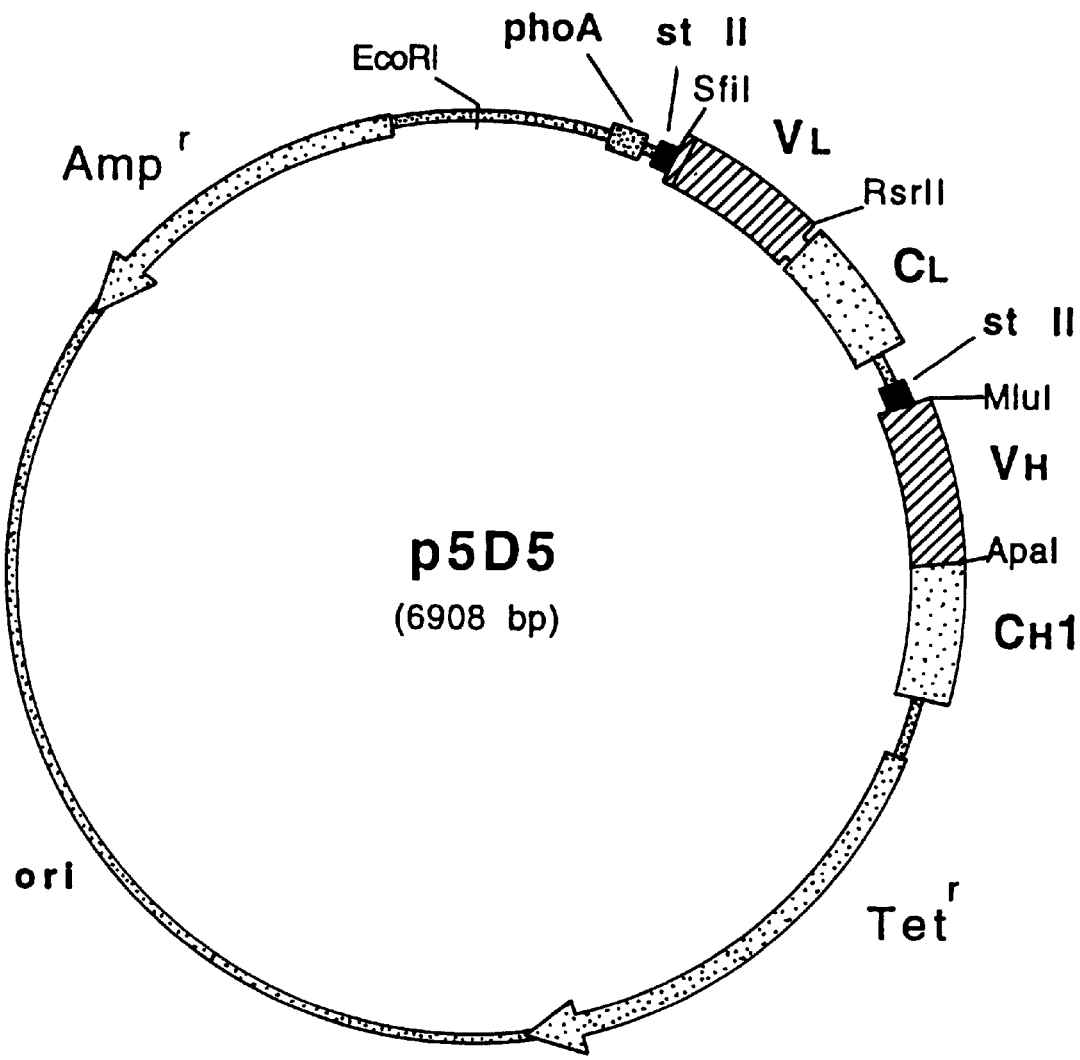
FIG. 12 is a restriction map of plasmid p5D5 containing the discistronic operon for expression of the chimer 5D5 Fab.

Recombinant 5D5 Fab was expressed in *E. coli* K12 strain 33B6 [Rodrigues et al., *Cancer Res.*, 55:63–70 (1995)], as described by Carter et al., supra. FIG. 12 shows a schematic representation of plasmid p5D5 containing the discistronic operon for expression of the chimer 5D5 Fab. Expression was under the control of the *E. coli* alkaline phosphatase promoter, which is inducible by phosphate starvation. Each antibody chain was preceded by the *E. coil* heat-stable enterotoxin II signal sequence to direct sequence to the periplasmic space of *E. coli*. The murine variable domains from antibody 5D5 ($V_L$ and $V_H$) were preciseiy fused on their 3' side to human $K_1$ $C_L$ and $C_{H1}$ constant domains, respectively.

The cell pellet from a 10-L fermentation was harvested by continuous feed centrifugation. frozen and stored at –70° C. A portion of the pellet was suspended in extraction buffer (120 mM MES, pH 6.0. and 5 mM EDTA, 5 ml/gram of paste). The suspension was mixed thoroughly using an ultraturrax (Janke and Kunkel) for approximately 15 minutes at 4° C. Intact cells were then disrupted using 2 passes through a cell homogenizer (Microfluidizer, by Microfluidics Corp., Newton, Mass.) fitted with a cooling coil. The suspension was then adjusted to 0.1% (v/v) polyethyleneimine using a 5% (v/v) stock which had been adjusted to pH 6.0. Intact cells and PEI-flocculated debris were separated from the soluble fraction by centrifugation at 25,400× g for 30 minutes. The supernatant was adjusted to a conductivity less than 4 mS by addition of purified water and loaded onto a column (1×10 cm) of Bakerbond ABX, 40 micron particle size (J. T. Baker, Phillipsburg, N.J.). The column had been equilibrated in 50 mM MES, 5 mM EDTA, pH 6.0. All steps were done at a linear flow rate of 100 cm/hour. After loading, the column was washed with equilibration buffer until the absorbance of the column effluent was equivalent to baseline. Elution was performed using a 16-column volume. linear gradient from 0 to 100 mM ammonium sulfate in equilibration buffer. Column fractions were analyzed by SDS-polyacrylamide gel electrophoresis and fractions which contained the Fab were pooled. The conductivity of the pool from the ABX column was lowered to less than 4 mS and loaded onto a column (1×10 cm) of SP-Sepharose High Performance resin (Pharmacia Biotech, Piscataway, N.J.) that had been equilibrated in 25 mM MOPS buffer, pH 6.9. All steps were performed at a linear flow rate of 100 cm/hour. Following the load, the column was washed with one column volume of equilibration buffer. The 5D5 Fab was then eluted from the column using a 16-column volume, linear gradient from 0 to 200 mM sodium acetate in equilibration buffer. Column fractions were analyzed by SDS-polyacrylamide gel electrophoresis and fractions which contained the Fab were pooled.

The light chain of the 5D5 Fab included amino acid residues 1 to 220, as shown in FIG. 1A (SEQ ID NO:1), and the heavy chain included amino acid residues 1 to 230 (wherein amino acid residue 1 comprised a glutamine acid residue), as shown in FIG. 1B (SEQ ID NO:2). Molecular weight analysis of the 5D5 Fab showed that it had a molecular weight of approximately 45 kDa. Although not fully understood, it is believed that amino acid residue 1 of native 5D5 Fab heavy chain may be a glutamine residue.

EXAMPLE 14

Assay of Recombinant 5D5 Fab Binding to c-Met

Figure 13:
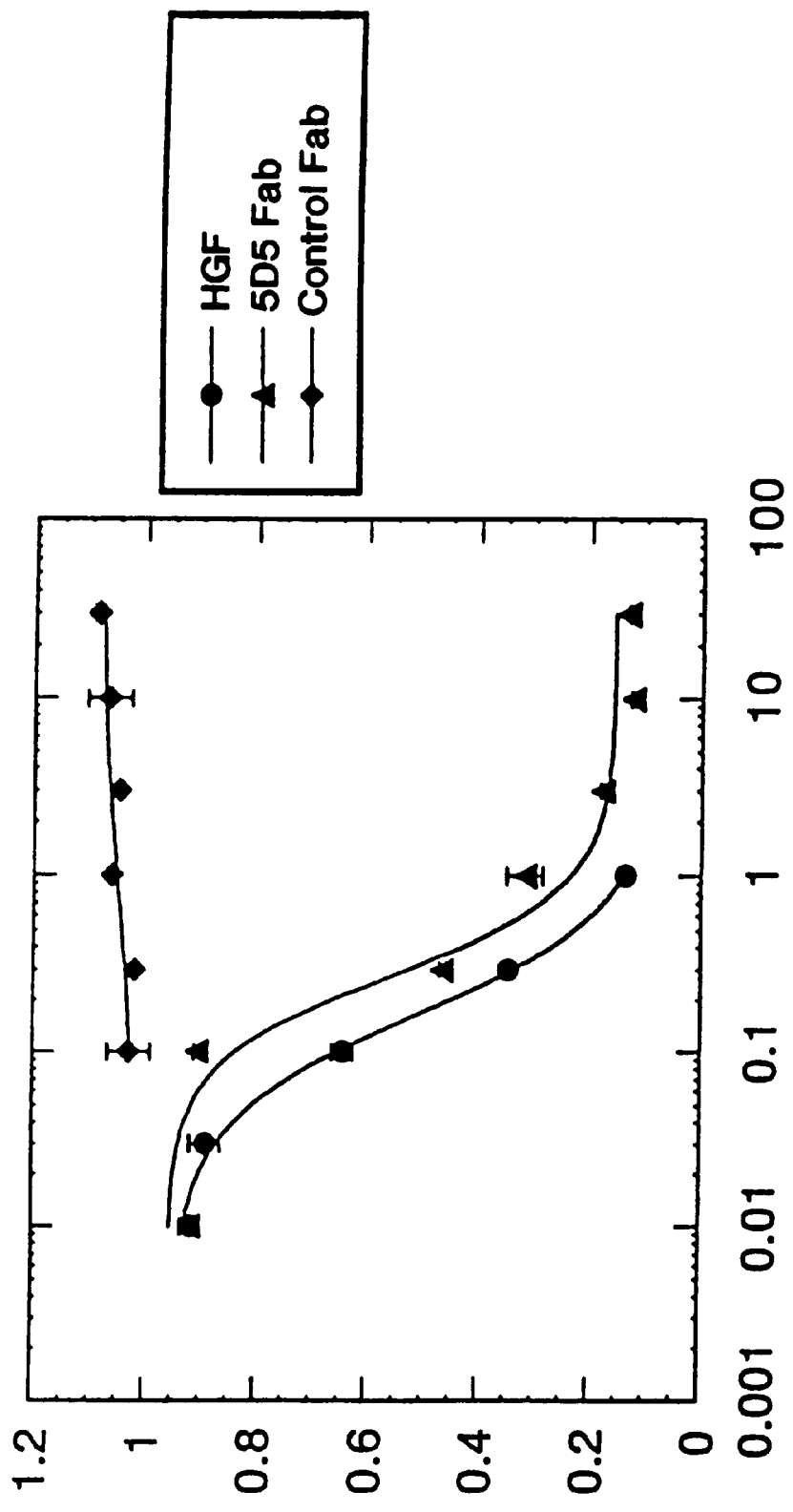
FIG. 13 is a graph showing the inhibition of HGF binding to c-Met-IgG fusion protein by recombinant 5D5 Fab.

An inhibition assay was conducted, essentially as described in Examples 3 and 8, to examine the ability of recombinant 5D5 Fab (Example 13) to block binding of HGF to c-Met-lgG fusion protein. rhuHGF, recombinant 5D5 Fab, or a recombinant control Fab (anti-VEGF Fab, Genentech, Inc.) were tested at concentrations ranging from 0.001–10 µg/ml, as shown in FIG. 13. The data, shown in FIG. 13, is the mean ±SD of duplicate wells. The graph in FIG. 13 illustrates that the recombinant 5D5 Fab inhibited HGF binding to c-Met while the control did not.

EXAMPLE 15

Effect of Heparin on Antagoniistic Activity of Recombinant 5D5 Fab

The effect of heparin on antagonistic activity of recombinant 5D5 Fab (Example 13) was examined using a thymidine incorporation assay as described in Examples 6, 9 and 11. BaF3-hmet cells were incubated with 0–10,000 ng/ml recombinant 5D5 Fab (Example 13) or recombinant control Fab alone (anti-VEGF Fab; described in Example 14), with 1 µg/ml heparin (Sigma), with 10 ng/ml rhuHGF, or with 10 ng/ml rhuHGF plus 1 µg/ml heparin.

The results are shown in FIGS. 14A–14D, and the data are the mean ±SEM of 4 replicates in a representative experiment. The results show that the recombinant 5D5 Fab remained an antagonist in the presence and absence of heparin.

Deposit of Materials

The following cultures have been deposited with the American Type Culture Collection, 10801 University Boulevard, Manassas, Va. 20110-2209, USA (ATCC);

| Hybridoma | ATCC No. | Deposit Date |
| --- | --- | --- |
| 1A3.3.13 | HB-11894 | May 23, 1995 |
| 5D5.11.6 | HB-11895 | May 23, 1995 |

This deposit was made under the provisions of the Budapest Treaty on the International Recognition of the Deposit of Microorganisms for the Purpose of Patent Procedure and the Regulations thereunder (Budapest Treaty). This assures maintenance of viable cultures for 30 years from the date of deposit. The organisms will be made available by ATCC under the terms of the Budapest Treaty, and subject to an agreement between Genentech, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the cultures on deposit should die or be lost or destroyed when cultivated under suitable conditions, they will be promptly replaced on notification with a viable specimen of the same culture. Availability of the deposited strains are not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the cultures deposited, since the deposited embodiments are intended as an illustration of an aspect of the invention and any cultures that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustration that it represents.

What is claimed is:

1. A method of treating cancer in a mammal, comprising administering an effective amount of HGF receptor antagonist which is a monovalent antibody that specifically binds to a HGF receptor to a mammal diagnosed as having cancer.

2. The method of claim 1 wherein said cancer is breast cancer.

3. The method of claim 1 wherein said cancer is pancreatic cancer.

4. The method of claim 1 wherein said cancer is colon cancer.

5. The method of claim 1 wherein said cancer is lung cancer.

6. An article of manufacture, comprising:
a container;
a label on said container; and
a composition contained within said container;

wherein the composition includes an active agent effective for treating cancer, the label on said container indicates that the composition can be used for treating cancer, and the active agent in said composition comprises HGF receptor antagonist which is a monovalent antibody that specifically binds to HGF receptor.

7. The article of manufacture of claim 6 further comprising instructions for administering the HGF receptor antagonist to a mammal.

8. A kit comprising:

a first container, a label on said container, and a composition contained within said container;

wherein the composition includes an active agent effective for treating cancer, the label on said container indicates that the composition can be used for treating cancer, and the active agent in said composition comprises HGF receptor antagonist which is a monovalent antibody that specifically binds to a HGF receptor;

a second container comprising a pharmaccutically-acceptable buffer; and instructions for using the HGF receptor antagonist to treat cancer.

9. An article of manufacture, comprising:

a container;

a label on said container; and a composition contained within said container;

wherein the composition includes an active agent effective for detecting or purifying HGF receptor, the label on said container indicates that the composition can be used for detecting or purifying HGF receptor, and the active agent in said composition comprises HGF receptor antagonist which is a monovalent antibody that specifically binds to HGF receptor.

10. A kit, comprising:

a first container, a label on said container, and a composition contained within said container;

wherein the composition includes an active agent effective for detecting or purifying HGF receptor, the label on said container indicates that the composition can be used for dctecting or purifying HGF receptor, and the active agent in said composition comprises HGF receptor antagonist which is a monovalent antibody that specifically binds to H-IGF receptor;

a second container comprising a pharmaceutically-acceptable buffer; and instructions for using the HGF receptor antagonist to detect or purify HGF receptor.

11. The method according to claim 1, wherein said HGF receptor is the c-Met receptor.

12. The method according to claim 11, wherein said monovalent antibody inhibits binding of human HGF to the c-Met receptor.

13. The method according to claim 1, wherein said monovalent antibody is a chimeric antibody having at least one domain of murine origin and at least one domain of human origin.

14. The method according to claim 1, wherein said monovalent antibody is a humanized antibody.

15. The method according to claim 1, wherein said monovalent antibody has all the identifying biological characteristics of a Fab fragment of the monoclonal antibody produced by the hybridoma cell line deposited under American Type Culture Collection Accession Number ATCC HB-11894.

16. The method according to claim 1, wherein said monovalent antibody binds to the same epitope as the epitope to which a Fab fragment of the monoclonal antibody produced by the hybridoma cell line deposited under American Type Culture Collection Accession Number ATCC HB-B 11894 binds.

17. The method according to claim 1, wherein said monovalent antibody has all the identifying biological characteristics of a Fab fragment of the monoclonal antibody produced by the hybridoma cell line deposited under American Type Culture Collection Accession Number ATCC HB-11895.

18. The method according to claim 1, wherein said monovalent antibody binds to the same epitope as the epitope to which a Fab fragment of the monoclonal antibody produced by the hybridoma cell line deposited under American Type Culture Collection Accession Number ATCC HB-1 1895 binds.

19. The method according to claim 1, wherein said monovalent antibody is a Fab fragment of a monoclonal antibody.

* * * * *

UNITED STATES PATENT AND TRADEMARK OFFICE
CERTIFICATE OF CORRECTION

PATENT NO. : 6,207,152 B1
DATED : March 27, 2001
INVENTOR(S) : Ralph H. Schwall et al.

It is certified that error appears in the above-identified patent and that said Letters Patent is hereby corrected as shown below:

Column 51,
Line 45, change "H-IGF" to -- HGF --.

Signed and Sealed this

Twenty-ninth Day of January, 2002

Attest:

Attesting Officer

JAMES E. ROGAN
Director of the United States Patent and Trademark Office